US008728092B2

(12) United States Patent
Qureshi et al.

(10) Patent No.: US 8,728,092 B2
(45) Date of Patent: May 20, 2014

(54) STEREOTACTIC DRIVE SYSTEM

(75) Inventors: Salman Qureshi, Winnipeg (CA); Mark Grant, Winnepeg (CA); Luis Filipe Silva Fernandes, Winnipeg (CA)

(73) Assignee: Monteris Medical Corporation, Plymouth, MN (US)

( * ) Notice: Subject to any disclaimer, the term of this patent is extended or adjusted under 35 U.S.C. 154(b) by 400 days.

(21) Appl. No.: 12/540,558

(22) Filed: Aug. 13, 2009

(65) Prior Publication Data
US 2010/0042112 A1 Feb. 18, 2010

Related U.S. Application Data

(60) Provisional application No. 61/088,969, filed on Aug. 14, 2008.

(51) Int. Cl.
*A61B 19/00* (2006.01)
(52) U.S. Cl.
USPC ........... 606/130; 606/131; 606/167; 606/153; 600/140; 600/142; 227/19; 227/179.1; 227/180.1
(58) Field of Classification Search
USPC ............... 600/140, 142; 227/19, 179.1, 180.1
See application file for complete search history.

(56) References Cited

U.S. PATENT DOCUMENTS

| 3,139,990 | A | * | 7/1964 | Jelatis et al. ........................ 414/2 |
| 4,111,209 | A | | 9/1978 | Wolvek et al. |
| 4,609,174 | A | | 9/1986 | Nakatani |
| 4,671,254 | A | | 6/1987 | Fair |
| 4,733,660 | A | | 3/1988 | Itzkan |
| 4,733,929 | A | | 3/1988 | Brown |
| 4,832,024 | A | | 5/1989 | Boussignac et al. |
| 4,914,608 | A | | 4/1990 | LeBiahan |
| 4,986,628 | A | | 1/1991 | Lozhenko et al. |

(Continued)

FOREIGN PATENT DOCUMENTS

| CA | 1317641 | 5/2011 |
| CN | 2620289 Y | 6/2004 |

(Continued)

OTHER PUBLICATIONS

Kahn, et al., Journal of Computer Assisted Tomography, vol. 18, No. 4, pp. 519-532, Jul./Aug. 1994, Raven Press, Ltd., New York, NY.

(Continued)

*Primary Examiner* — Katherine Dowe
*Assistant Examiner* — Sidharth Kapoor
(74) *Attorney, Agent, or Firm* — Oblon, Spivak, McClelland, Maier & Neustadt, L.L.P.

(57) ABSTRACT

A drive system for controlling movement of an elongate member includes a base unit having a first rotatable knob and a second rotatable knob, a follower assembly including a follower slidably coupled to a guide rail, a longitudinal movement wire, and a rotational movement wire. The follower includes a longitudinal movement pulley, a rotational movement pulley, and an alignment element structured to receive an elongate member such that the elongate member is attachable thereto. The longitudinal movement wire operably couples the first rotatable knob to the longitudinal movement pulley such that rotation of the first knob drives the follower in a longitudinal direction along the guide rail. The rotational movement wire operably couples the second rotatable knob to the rotational movement pulley such that rotation of the second knob rotates the alignment element and attached elongate member.

23 Claims, 15 Drawing Sheets

(56) References Cited

U.S. PATENT DOCUMENTS

| | | |
|---|---|---|
| 5,102,410 A | 4/1992 | Dressel |
| 5,116,344 A | 5/1992 | Sundqvist |
| 5,154,723 A | 10/1992 | Kubota et al. |
| 5,196,005 A | 3/1993 | Doiron et al. |
| 5,201,742 A | 4/1993 | Hasson |
| 5,207,669 A | 5/1993 | Baker et al. |
| 5,207,681 A | 5/1993 | Ghadjar et al. |
| 5,230,338 A | 7/1993 | Allen et al. |
| 5,242,438 A | 9/1993 | Saadatmanesh et al. |
| 5,246,436 A | 9/1993 | Rowe |
| 5,247,935 A | 9/1993 | Cline et al. |
| 5,263,956 A | 11/1993 | Nobles |
| 5,269,777 A | 12/1993 | Doiron et al. |
| 5,281,213 A | 1/1994 | Milder et al. |
| 5,284,144 A | 2/1994 | Delannoy |
| 5,291,890 A | 3/1994 | Cline et al. |
| 5,292,320 A | 3/1994 | Brown et al. |
| 5,307,144 A | 4/1994 | Hiroshi et al. |
| 5,307,812 A | 5/1994 | Hardy et al. |
| 5,320,617 A | 6/1994 | Leach |
| 5,327,884 A | 7/1994 | Hardy et al. |
| 5,343,543 A | 8/1994 | Noval, Jr. et al. |
| 5,344,419 A | 9/1994 | Spears |
| 5,354,293 A | 10/1994 | Beyer et al. |
| 5,354,294 A | 10/1994 | Chou |
| 5,366,456 A | 11/1994 | Rink et al. |
| 5,368,031 A | 11/1994 | Cline et al. |
| 5,370,649 A | 12/1994 | Gardetto et al. |
| 5,374,266 A | 12/1994 | Kataoka et al. |
| 5,387,220 A | 2/1995 | Pisharodi |
| 5,433,717 A * | 7/1995 | Rubinsky et al. ............... 606/20 |
| 5,445,166 A | 8/1995 | Taylor |
| 5,454,794 A | 10/1995 | Narciso et al. |
| 5,454,807 A | 10/1995 | Lennox |
| 5,454,897 A | 10/1995 | Vaniglia |
| 5,474,564 A | 12/1995 | Clayman et al. |
| 5,492,122 A | 2/1996 | Button et al. |
| 5,496,308 A | 3/1996 | Brown et al. |
| 5,509,917 A | 4/1996 | Cecchetti et al. |
| 5,530,780 A | 6/1996 | Ohsawa |
| 5,534,000 A | 7/1996 | Bruce |
| 5,537,499 A | 7/1996 | Brekke |
| 5,568,503 A | 10/1996 | Omori |
| 5,571,099 A | 11/1996 | Purcell, Jr. et al. |
| 5,620,479 A | 4/1997 | Diederich |
| 5,632,767 A | 5/1997 | Sinofsky |
| 5,638,819 A | 6/1997 | Manwaring et al. |
| 5,672,172 A | 9/1997 | Zupkas |
| 5,695,501 A | 12/1997 | Carol et al. |
| 5,719,975 A | 2/1998 | Wolfson et al. |
| 5,733,277 A | 3/1998 | Pallarito |
| 5,749,362 A | 5/1998 | Funda et al. |
| 5,749,549 A | 5/1998 | Ashjaee |
| 5,752,962 A | 5/1998 | D'Urso |
| 5,762,066 A | 6/1998 | Law et al. |
| 5,772,657 A | 6/1998 | Hmelar et al. |
| 5,785,704 A | 7/1998 | Bille |
| 5,792,110 A | 8/1998 | Cunningham |
| 5,807,383 A | 9/1998 | Kolesa et al. |
| 5,823,941 A | 10/1998 | Shaunnessey |
| 5,824,005 A | 10/1998 | Motamedi et al. |
| 5,848,967 A | 12/1998 | Cosman |
| 5,855,583 A * | 1/1999 | Wang et al. ............... 606/139 |
| 5,861,020 A | 1/1999 | Schwarzmaier |
| 5,868,760 A * | 2/1999 | McGuckin, Jr. ............... 606/139 |
| 5,891,157 A | 4/1999 | Day et al. |
| 5,947,958 A | 9/1999 | Woodard et al. |
| 5,949,929 A | 9/1999 | Hamm |
| 5,959,246 A | 9/1999 | Gretz |
| 5,978,541 A | 11/1999 | Doiron et al. |
| 5,989,246 A | 11/1999 | Kaufmann et al. |
| 5,993,463 A | 11/1999 | Truwit |
| 6,004,315 A | 12/1999 | Dumont |
| 6,006,126 A | 12/1999 | Cosman |
| 6,022,309 A | 2/2000 | Celliers et al. |
| 6,039,728 A | 3/2000 | Berlien et al. |
| 6,058,323 A | 5/2000 | Lemelson |
| 6,071,288 A | 6/2000 | Carol et al. |
| 6,086,532 A | 7/2000 | Panescu et al. |
| 6,106,516 A | 8/2000 | Massengill |
| 6,117,143 A | 9/2000 | Hynes et al. |
| 6,123,719 A | 9/2000 | Masychev |
| 6,128,522 A | 10/2000 | Acker et al. |
| 6,131,480 A | 10/2000 | Yoneyama |
| 6,132,437 A | 10/2000 | Omurtag et al. |
| 6,162,052 A | 12/2000 | Kokubu |
| 6,164,843 A | 12/2000 | Battocchio |
| 6,167,295 A | 12/2000 | Cosman |
| 6,206,873 B1 | 3/2001 | Paolini et al. |
| 6,206,885 B1 | 3/2001 | Ghahremani et al. |
| 6,206,890 B1 | 3/2001 | Truwit |
| 6,246,200 B1 * | 6/2001 | Blumenkranz et al. .. 318/568.11 |
| 6,246,896 B1 | 6/2001 | Dumoulin et al. |
| 6,254,043 B1 | 7/2001 | Schwärzler |
| 6,267,769 B1 | 7/2001 | Truwit |
| 6,267,770 B1 | 7/2001 | Truwit |
| 6,280,384 B1 | 8/2001 | Loeffler |
| 6,283,958 B1 | 9/2001 | Vogl et al. |
| 6,286,795 B1 | 9/2001 | Johnson |
| 6,293,282 B1 | 9/2001 | Lemelson |
| 6,332,891 B1 | 12/2001 | Himes |
| 6,355,028 B2 | 3/2002 | Castaneda et al. |
| 6,368,329 B1 | 4/2002 | Truwit |
| 6,368,330 B1 | 4/2002 | Hynes et al. |
| 6,398,778 B1 | 6/2002 | Gu et al. |
| 6,413,253 B1 | 7/2002 | Koop |
| 6,413,263 B1 | 7/2002 | Lobdill et al. |
| 6,416,520 B1 | 7/2002 | Kynast et al. |
| 6,418,337 B1 | 7/2002 | Torchia |
| 6,423,077 B2 | 7/2002 | Carol et al. |
| 6,425,867 B1 | 7/2002 | Vaezy et al. |
| 6,464,690 B1 | 10/2002 | Castaneda et al. |
| 6,464,691 B1 | 10/2002 | Castaneda et al. |
| 6,491,699 B1 | 12/2002 | Henderson et al. |
| 6,529,765 B1 | 3/2003 | Franck et al. |
| 6,544,248 B1 | 4/2003 | Bass |
| 6,551,274 B2 | 4/2003 | Heiner |
| 6,558,375 B1 | 5/2003 | Sinofsky et al. |
| 6,579,281 B2 | 6/2003 | Palmer et al. |
| 6,582,420 B2 | 6/2003 | Castaneda et al. |
| 6,589,174 B1 | 7/2003 | Chopra et al. |
| 6,589,233 B1 | 7/2003 | Maki |
| 6,695,871 B1 | 2/2004 | Maki et al. |
| 6,701,181 B2 | 3/2004 | Tang et al. |
| 6,716,215 B1 | 4/2004 | David et al. |
| 6,741,883 B2 | 5/2004 | Gildenberg |
| 6,752,812 B1 | 6/2004 | Truwit |
| 6,782,288 B2 | 8/2004 | Truwit et al. |
| 6,843,793 B2 * | 1/2005 | Brock et al. ............... 606/130 |
| 6,845,193 B2 | 1/2005 | Loeb et al. |
| 6,893,447 B2 | 5/2005 | Dominguez et al. |
| 6,902,569 B2 | 6/2005 | Parmer et al. |
| 6,986,764 B2 | 1/2006 | Davenport et al. |
| 7,033,367 B2 | 4/2006 | Ghahremani et al. |
| 7,072,704 B2 | 7/2006 | Bucholz |
| 7,167,741 B2 | 1/2007 | Torchia et al. |
| 7,167,760 B2 | 1/2007 | Dawant et al. |
| 7,235,084 B2 | 6/2007 | Skakoon et al. |
| 7,235,089 B1 | 6/2007 | McGuckin, Jr. |
| 7,270,656 B2 | 9/2007 | Gowda et al. |
| 7,344,529 B2 | 3/2008 | Torchia et al. |
| 7,366,561 B2 | 4/2008 | Mills et al. |
| 7,371,210 B2 | 5/2008 | Brock et al. |
| 7,463,801 B2 | 12/2008 | Brekke et al. |
| 7,479,139 B2 | 1/2009 | Cytron et al. |
| 7,736,371 B2 | 6/2010 | Schoepp |
| 7,794,469 B2 | 9/2010 | Kao et al. |
| 8,114,068 B2 | 2/2012 | Rheinwald et al. |
| 8,165,658 B2 | 4/2012 | Waynik et al. |
| 8,267,938 B2 | 9/2012 | Murphy |
| 8,285,097 B2 | 10/2012 | Griffin |
| 8,298,245 B2 | 10/2012 | Li et al. |
| 8,414,597 B2 | 4/2013 | Kao et al. |
| 2002/0019641 A1 | 2/2002 | Truwit |

(56) References Cited

U.S. PATENT DOCUMENTS

| | | |
|---|---|---|
| 2002/0052610 A1 | 5/2002 | Skakoon et al. |
| 2002/0169460 A1 | 11/2002 | Foster et al. |
| 2002/0177843 A1 | 11/2002 | Andersen et al. |
| 2003/0060813 A1 | 3/2003 | Loeb et al. |
| 2003/0171741 A1 | 9/2003 | Ziebol et al. |
| 2004/0075031 A1 | 4/2004 | Crain et al. |
| 2004/0122446 A1 | 6/2004 | Solar |
| 2004/0133190 A1 | 7/2004 | Hobart et al. |
| 2004/0134884 A1 | 7/2004 | Wei et al. |
| 2004/0167542 A1 | 8/2004 | Solar et al. |
| 2004/0167543 A1 | 8/2004 | Mazzocchi et al. |
| 2004/0267284 A1 | 12/2004 | Parmer et al. |
| 2005/0070920 A1 | 3/2005 | Solar et al. |
| 2005/0154378 A1 | 7/2005 | Teague et al. |
| 2006/0009749 A1 | 1/2006 | Weckwerth et al. |
| 2006/0089626 A1 | 4/2006 | Vlegele et al. |
| 2006/0122590 A1 | 6/2006 | Bliweis et al. |
| 2006/0122629 A1 | 6/2006 | Skakoon |
| 2006/0175484 A1 | 8/2006 | Wood, III et al. |
| 2006/0192319 A1 | 8/2006 | Solar et al. |
| 2006/0195119 A1 | 8/2006 | Mazzocchi et al. |
| 2006/0206105 A1 | 9/2006 | Chopra et al. |
| 2006/0212044 A1 | 9/2006 | Bova et al. |
| 2006/0229641 A1 | 10/2006 | Gupta et al. |
| 2006/0287647 A1 | 12/2006 | Torchia et al. |
| 2007/0043342 A1 | 2/2007 | Kleinberger |
| 2007/0100346 A1 | 5/2007 | Wyss et al. |
| 2007/0106305 A1 | 5/2007 | Kao et al. |
| 2007/0149977 A1 | 6/2007 | Heavener |
| 2007/0191867 A1 | 8/2007 | Mazzocchi et al. |
| 2007/0208352 A1 | 9/2007 | Henderson et al. |
| 2007/0225562 A1* | 9/2007 | Spivey et al. ............... 600/121 |
| 2007/0239062 A1 | 10/2007 | Chopra et al. |
| 2007/0250077 A1 | 10/2007 | Skakoon et al. |
| 2007/0270717 A1 | 11/2007 | Tang et al. |
| 2008/0002927 A1 | 1/2008 | Furnish |
| 2008/0027463 A1 | 1/2008 | Labadie et al. |
| 2008/0046122 A1* | 2/2008 | Manzo et al. ............... 700/245 |
| 2008/0077159 A1 | 3/2008 | Madhani et al. |
| 2008/0097187 A1 | 4/2008 | Gielen et al. |
| 2008/0123921 A1 | 5/2008 | Gielen et al. |
| 2008/0123922 A1 | 5/2008 | Gielen et al. |
| 2008/0195085 A1 | 8/2008 | Loeb |
| 2008/0242978 A1 | 10/2008 | Simon et al. |
| 2008/0243142 A1 | 10/2008 | Gildenberg |
| 2008/0255583 A1 | 10/2008 | Gielen et al. |
| 2008/0269588 A1 | 10/2008 | Csavoy et al. |
| 2008/0269602 A1 | 10/2008 | Csavoy et al. |
| 2008/0287917 A1 | 11/2008 | Cunningham |
| 2008/0306375 A1 | 12/2008 | Sayler et al. |
| 2009/0012509 A1 | 1/2009 | Csavoy et al. |
| 2009/0048588 A1 | 2/2009 | Peng et al. |
| 2009/0112082 A1 | 4/2009 | Piferi et al. |
| 2009/0118610 A1 | 5/2009 | Karmarkar et al. |
| 2009/0124398 A1* | 5/2009 | Thompson ............... 464/52 |
| 2009/0131783 A1 | 5/2009 | Jenkins et al. |
| 2009/0198309 A1 | 8/2009 | Gowda et al. |
| 2009/0204111 A1 | 8/2009 | Bissig et al. |
| 2009/0240242 A1 | 9/2009 | Neuberger |
| 2009/0287199 A1 | 11/2009 | Hanley et al. |
| 2009/0326525 A1 | 12/2009 | Hixon et al. |
| 2010/0041938 A1 | 2/2010 | Stoianovici et al. |
| 2010/0042112 A1 | 2/2010 | Qureshi et al. |
| 2010/0082035 A1 | 4/2010 | Keefer |
| 2011/0040172 A1 | 2/2011 | Carpentier et al. |
| 2011/0118715 A1 | 5/2011 | Zerfas |
| 2011/0141759 A1 | 6/2011 | Smith |
| 2011/0166447 A1 | 7/2011 | Windolf et al. |
| 2011/0190787 A1 | 8/2011 | Sahni et al. |
| 2011/0217665 A1 | 9/2011 | Walsh et al. |
| 2011/0301450 A1 | 12/2011 | Hue et al. |
| 2012/0053573 A1 | 3/2012 | Alksnis |
| 2013/0018430 A1 | 1/2013 | Murphy |
| 2013/0041356 A1 | 2/2013 | Smith et al. |
| 2013/0060253 A1 | 3/2013 | Couture et al. |
| 2013/0085342 A1 | 4/2013 | Stefanchik et al. |

FOREIGN PATENT DOCUMENTS

| | | |
|---|---|---|
| CN | 2748071 Y | 12/2005 |
| CN | 101040772 A | 9/2007 |
| CN | 101194853 A | 6/2008 |
| EP | 0 610 991 A2 | 8/1994 |
| EP | 0 614 651 A1 | 9/1994 |
| EP | 0 755 697 A2 | 1/1997 |
| EP | 1829764 A2 | 9/2007 |
| EP | 1985330 A1 | 10/2008 |
| JP | 7-308393 | 11/1995 |
| JP | 9-038220 | 2/1997 |
| JP | 10-155805 | 6/1998 |
| JP | 11-253562 | 9/1999 |
| JP | 2000-000319 | 1/2000 |
| JP | 2000-126316 | 5/2000 |
| JP | 2002-543865 | 12/2002 |
| WO | WO 90/05494 | 5/1990 |
| WO | WO 93/20769 | 10/1993 |
| WO | WO 94/04220 | 3/1994 |
| WO | WO 98/51229 | 11/1998 |
| WO | WO 98/52465 | 11/1998 |
| WO | WO 99/51156 | 10/1999 |
| WO | WO 00/23000 | 4/2000 |
| WO | WO 00/67640 | 11/2000 |
| WO | WO 01/76498 A3 | 10/2001 |
| WO | WO 03/094759 A1 | 11/2003 |
| WO | WO 2004/075722 A2 | 9/2004 |
| WO | WO 2005/046451 A2 | 5/2005 |
| WO | WO 2007/056458 A2 | 5/2007 |
| WO | WO 2007/060474 A1 | 5/2007 |
| WO | WO/2007/064937 | 6/2007 |
| WO | WO 2008/070685 | 6/2008 |

OTHER PUBLICATIONS

Kahn, et al., Journal of Magnetic Resonance Imaging, vol. 8, No. 1, pp. 160-164, Williams & Wilkins, 1998, Baltimore, MD.

Vogl, et al., in "Internally Cooled Power Laser for MR-guided Interstitial Laser-induced Thermotherapy of Liver Lasions: Initial Clinical Results", in Radiology, 1998, 209: pp. 381-385.

McNichols, et al., "MR Thermometry-Based Feedback Control of Laser Interstitial Thermal Therapy at 980 nm", Lasers in Surgery and Medicine, 2004, 34: 48-55, Wiley-Liss, Inc.

International Preliminary Report on Patentability, dated Feb. 15, 2011, regarding PCT/CA2009/001138, 5 pgs.

Office Action mailed Nov. 1, 2012, in Japanese Patent Application No. 2011-522361 (with English-language translation).

Combined Chinese Office Action and Search Report issued Mar. 13, 2013, in Patent Application No. 200980131609.X (with English-language translation).

Office Action mailed Jul. 17, 2013, in Japanese Patent Application No. 2011-522361 (with English-language translation).

Office Action mailed Jul. 29, 2013, in Japanese Patent Application No. 2011-522360 (with English-language translation).

Search Report dated Oct. 18, 2013, in European Patent Application No. 09806277.1.

International Search Report and Written Opinion mailed Jun. 10, 2013, in PCT/US13/32273.

International Preliminary Report on Patentability mailed Feb. 15, 2011, in PCT/CA2009/01137, 8 pages.

Office Action mailed Oct. 25, 2011, in Brazilian Patent Application No. PI-0214951-6 (English translation).

Office Action mailed May 28, 2013, in Brazilian Patent Application No. PI-0214951-6 (English translation).

(56) References Cited

OTHER PUBLICATIONS

Schwarzmaier et al., "MR-guided laser-induced interstitial thermotherapy of recurrent glioblastoma multiforme: Preliminary results in 16 patients," European Journal of Radiology, vol. 59, Issue 2, pp. 208-215, Aug. 2006.

Office Action mailed Dec. 27, 2013, in Israeli Patent Application No. 210878.

Office Action mailed Aug. 22, 2013, in Chinese Patent Application No. 200980131600.9 (with English-language translation).

Office Action issued in Chinese Patent Application No. 200980131609.X on Jan. 10, 2014.

Office Action mailed Feb. 28, 2014, in co-pending U.S. Appl. No. 13/932,725, pp. 1-23.

\* cited by examiner

STEREOTACTIC DRIVE SYSTEM

CROSS-REFERENCE TO RELATED APPLICATION(S)

This application claims the benefit of U.S. Provisional Application Ser. No. 61/088,969, filed Aug. 14, 2008, the entirety of which is hereby incorporated by reference.

BACKGROUND OF THE INVENTION

The present invention relates generally to control systems. More specifically, the present invention relates to a drive system for controlling the longitudinal movement and rotational position of an elongate member.

Each year roughly 200,000 patients are diagnosed with brain tumors in the United States. Roughly 17,000 of these tumors are "benign," meaning that the tumor mass is not cancerous. However, the other roughly 183,000 of these tumors are "malignant" (i.e., cancerous), meaning that they are capable of causing or contributing to patient death. Approximately 10% of cancerous brain tumors are "primary" tumors, meaning that the tumors originate in the brain. The primary tumors typically consist of brain tissue with mutated DNA that aggressively grows and displaces or replaces normal brain tissue. The most common of the primary tumors are known as gliomas, which indicate cancer of the glial cells of the brain. In most instances, primary tumors appear as single masses. However, these single masses can often be quite large, irregularly-shaped, multi-lobed and/or infiltrated into surrounding brain tissue.

Primary tumors are generally not diagnosed until the patient experiences symptoms, such as headaches, altered behavior, sensory impairment, or the like. However, by the time the symptoms develop the tumor may already be large and aggressive.

One well known treatment for cancerous brain tumors is surgery. In particular, surgery involves a craniotomy (i.e., removal of a portion of the skull), dissection, and total or partial tumor resection. The objectives of surgery include removal or lessening of the number of active malignant cells within the brain, and a reduction in the pain or functional impairment due to the effect of the tumor on adjacent brain structures. However, by its very nature, surgery is highly invasive and risky. Furthermore, for some tumors surgery is often only partially effective. In other tumors, the surgery itself may not be feasible, it may risk impairment to the patient, it may not be tolerable by the patient, and/or it may involve significant cost and recovery.

Another well known treatment for cancerous brain tumors is stereotactic radiosurgery (SRS). In particular, SRS is a treatment method by which multiple intersecting beams of radiation are directed at the tumor such that the point of intersection of the beams receives a lethal dose of radiation, while tissue in the path of any single beam remains unharmed. SRS is non-invasive and is typically performed as a single outpatient procedure. However, confirmation that the tumor has been killed or neutralized is often not possible for several months post-treatment. Furthermore, in situations where high doses of radiation may be required to kill a tumor, such as in the case of multiple or recurring tumors, it is common for the patient to reach the "toxic threshold" prior to killing all of the tumors, where further radiation is inadvisable.

More recently, the treatment of tumors by "heat" (also referred to as hyperthermia or thermal therapy) has been developed. In particular, it is known that above 57° C. all living tissue is almost immediately and irreparably damaged and killed through a process called coagulation necrosis or ablation. Malignant tumors, because of their high vascularization and altered DNA, are more susceptible to heat-induced damage than normal tissue. Various types of energy sources may be used, such as laser, microwave, radiofrequency, electric, and ultrasound sources. Depending upon the application and the technology, the heat source may be extracorporeal (i.e., outside the body), extrastitial (i.e., outside the tumor), or interstitial (i.e., inside the tumor).

Interstitial thermal therapy (ITT) is a process designed to heat and destroy a tumor from within the tumor. One advantage of this type of therapy is that the energy is applied directly to the tumor rather than passing through surrounding normal tissue. Another advantage of the type of therapy is that the energy deposition is more likely to be extended throughout the entire tumor.

One exemplary ITT process begins by inserting an optical fiber into the tumor, wherein the tumor has an element at its "inserted" end that redirects laser light from an exterior source in a direction generally at right angles to the length of the fiber. The energy from the laser thus extends into the tissue surrounding the end or tip and effects heating. The energy is directed in a beam confined to a relatively shallow angle so that, as the fiber is rotated, the beam also rotates around the axis of the fiber to effect heating of different parts of the tumor at positions around the fiber. The fiber can thus be moved longitudinally and rotated to effect heating of the tumor over the full volume of the tumor with the intention of heating the tumor to the required temperature without significantly affecting the surrounding tissue.

The fiber used in the ITT process may be controlled and manipulated by a surgeon with little or no guidance apart from the surgeon's knowledge of the anatomy of the patient and the location of the tumor. Therefore, it is difficult for the surgeon to effect a controlled heating which heats the entire tumor to a required level while also minimizing damage to the surrounding tissue.

It is known that the location of tumors and other lesions to be excised can be determined using a magnetic resonance imaging system. Although these imaging systems have been helpful to assist the surgeon in determining a location of the tumor to be excised, use of the imaging systems ended once the location of the tumor was mapped out for the surgeon. In particular, previous excision procedures required the removal of the patient from the imaging system prior to commencing treatment. However, movement of the patient, together with the partial excision or coagulation of some of the tissue, can significantly change the location of the tumor to be excised. As a result, any possibility of providing controlled accuracy in the excision is eliminated.

It is also known that magnetic resonance imaging systems can be used by modification of the imaging sequences to determine the temperature of tissue within the image and to determine changes in that temperature over time.

U.S. Pat. No. 4,914,608 (LeBiahan) assigned to U.S. Department of Health and Human Services issued Apr. 3, 1990, discloses a method for determining temperature in tissue.

U.S. Pat. No. 5,284,144 (Delannoy) also assigned to U.S. Department of Health and Human Services and issued Feb. 8, 1994, discloses an apparatus for hyperthermia treatment of cancer in which an external, non-invasive heating system is mounted within the coil of a magnetic resonance imaging system. The disclosure is speculative and relates to initial experimentation concerning the viability of MRI measurement of temperature in conjunction with an external heating system. The disclosure of the patent has not led to a commercially viable hyperthermic treatment system.

U.S. Pat. Nos. 5,368,031 and 5,291,890 assigned to General Electric relate to an MRI controlled heating system in which a point source of heat generates a predetermined heat distribution which is then monitored to ensure that the actual heat distribution follows the predicted heat distribution to obtain an overall heating of the area to be heated. Again this patented arrangement has not led to a commercially viable hyperthermia surgical system.

U.S. Pat. No. 4,671,254 (Fair) assigned to Memorial Hospital for Cancer and Allied Diseases and issued Jun. 9, 1987, discloses a method for the non surgical treatment of tumors in which the tumor is subjected to shock waves. This type of treatment does not incorporate a monitoring system to monitor and control the effect of the shock waves.

U.S. Pat. No. 5,823,941 (Shaunnessey), not assigned, and issued Oct. 20, 1998, discloses a specially modified endoscope designed to support an optical fiber. The optical fiber emits light energy and may be moved longitudinally and rotated angularly about its axis to direct the energy. The device is used for excising tumors, and the energy is arranged to be sufficient to effect vaporization of the tissue to be excised. The gas formed during the process is removed by suction through the endoscope. An image of the tumor is obtained by MRI, which is thereafter used to program a path of movement of the fiber to be taken during the operation. Again, there is no feedback during the procedure to control the movement of the optical fiber, and the operation is wholly dependent upon the initial analysis. This arrangement has not achieved commercial or medical success.

U.S. Pat. No. 5,454,807 (Lennox) assigned to Boston Scientific Corporation and issued Oct. 3, 1995, discloses a device for use in irradiating a tumor with light energy from an optical fiber. A cooling fluid is supplied through a conduit within the fiber to apply surface cooling and to prevent surface damage while allowing increased levels of energy to be applied to deeper tissues. Once again, this arrangement does not provide feedback control of the heating effect.

U.S. Pat. No. 5,785,704 (Bille) assigned to MRC Systems GmbH and issued Jul. 28, 1996, also discloses a particular arrangement of a laser beam and lens for use in irradiation of brain tumors. In particular, this arrangement uses high speed pulsed laser energy for a photo-disruption effect, but does not disclose methods of feedback control of the energy.

Kahn, et al. in Journal of Computer Assisted Tomography 18(4):519-532, July/August 1994; Kahn, et al. in Journal of Magnetic Resonance Imaging 8: 160-164, 1998; and Vogl, et al. in Radiology 209: 381-385, 1998, all disclose a method of application of heat energy from a laser through a fiber to a tumor where the temperature at the periphery of the tumor is monitored during the application of the energy by MRI. McNichols, R J et al. in Lasers in Surgery and Medicine, 34:48-55, 2005, disclose energy control by an MRI feedback monitoring arrangement in a paper entitled "MR Thermometry-Based Feedback Control of LITT at 980 nm." Additionally, the paper of Vogl discloses a cooling system supplied commercially by Somatex of Berlin, Germany for cooling the tissues at the probe end. The system is formed by an inner tube containing the fiber mounted within an outer tube. Cooling fluid is passed between the two tubes and inside the inner tube in a continuous stream.

While highly effective in certain applications, the use of ITT to treat brain tumors has been limited by the inability to focus the energy exclusively and precisely on the tumor so as to avoid damage to surrounding normal brain tissue. This is complicated by the fact that many brain tumors are highly irregular in shape.

Focused laser interstitial thermal therapy (f-LITT) is the next general refinement of laser-based thermal therapy technologies. In particular, f-LITT enables precise control over the deposition of heat energy, thereby enabling the physician to contain cell damage exclusively to within a tumor mass of virtually any size and shape. However, as with other ITT treatment systems, there is a need for an apparatus that allows a surgeon to precisely control the position of the treatment device within the tumor mass.

Therefore, a heretofore unaddressed need exists to establish a drive system for an elongate member that is capable of precisely controlling both the longitudinal and rotational positions of the elongate member with respect to a target, such as a tumor mass. Furthermore, what is needed is a drive system for an elongate member that is simple to use and that yields accurate and predictable results. The drive system should preferably be structured for use with any elongate medical device including, but not limited to, laser probes, catheters, endoscopes, and the like. The drive system should also preferably be manufactured from materials that make the system MRI-compatible.

SUMMARY OF THE INVENTION

The present invention solves the foregoing problems by providing a drive system for controlling movement of an elongate member including a base unit having a first rotatable knob and a second rotatable knob, a follower assembly including a follower slidably coupled to a guide rail, a longitudinal movement wire, and a rotational movement wire. The follower includes a longitudinal movement pulley, a rotational movement pulley, and an alignment element structured to receive an elongate member such that the elongate member is attachable thereto. The longitudinal movement wire operably couples the first rotatable knob to the longitudinal movement pulley such that rotation of the first knob drives the follower in a longitudinal direction along the guide rail. The rotational movement wire operably couples the second rotatable knob to the rotational movement pulley such that rotation of the second knob rotates the alignment element and attached elongate member.

DETAILED DESCRIPTION OF THE INVENTION

The present invention involves a drive system for stereotactic positioning of an elongate member. The elongate member may include, for example, elongate probes, catheters, endoscopes, and the like. However, those skilled in the art will appreciate that the drive system of the present invention may be used in conjunction with any elongate member requiring precise control in a longitudinal and/or rotational direction.

In one exemplary embodiment, the drive system in accordance with the present invention may be used to control the precise movement of a laser probe insertable into the skull of a patient for the treatment of tumors. In particular, and as will be evident to one skilled in the art based upon the following disclosure and corresponding figures, the drive system may be operated to position a distal end of a probe at precise locations within the tumor through both controlled longitudinal and rotational movement of the probe.

Figure 1:
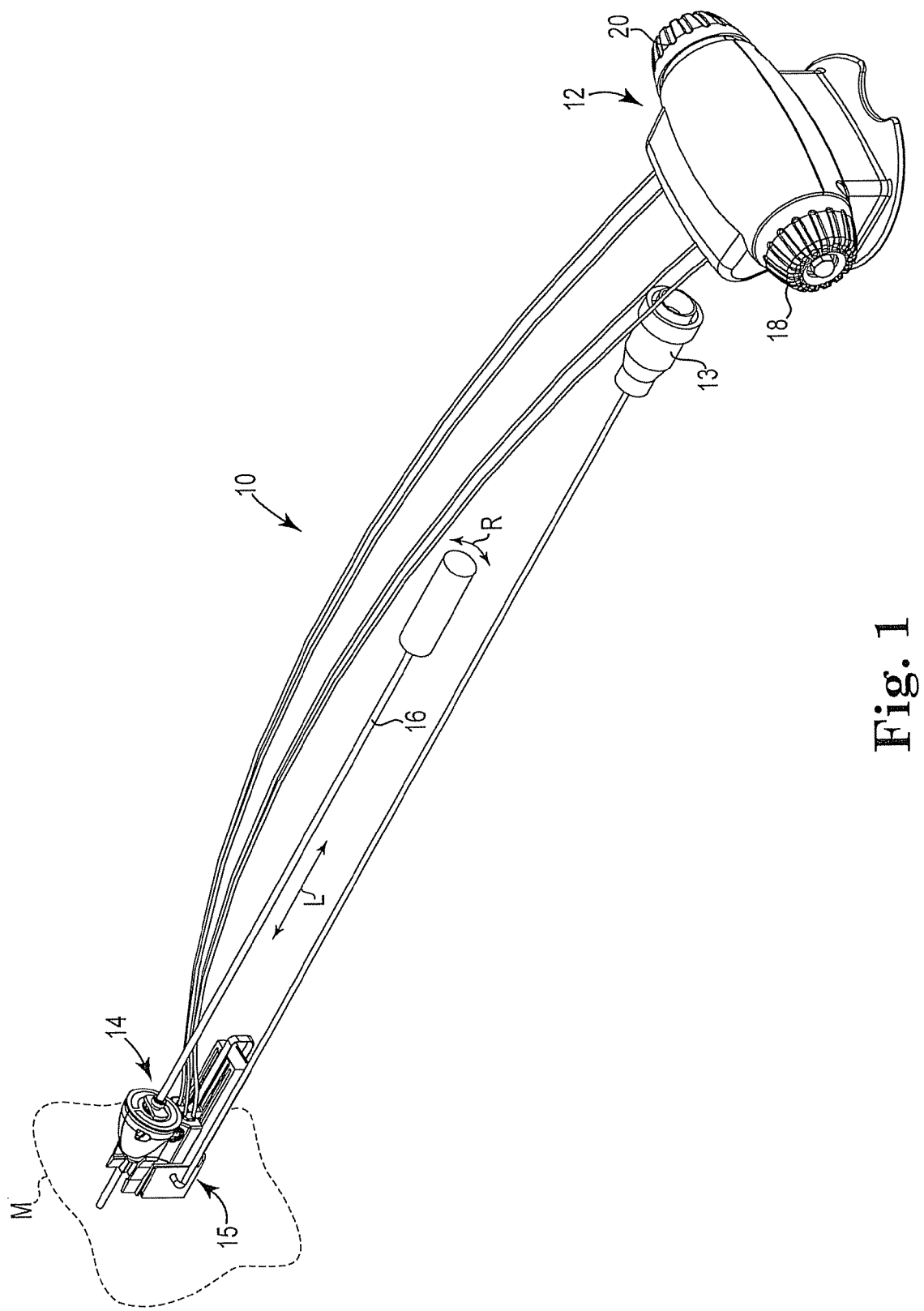
FIG. 1 is a perspective view of one exemplary drive system in accordance with the present invention that includes a commander unit, a follower assembly, and an elongate member coupled to the follower assembly.

Referring now to FIG. 1, there is shown a perspective view of one exemplary drive system 10 including commander or base unit 12, follower assembly 14, potentiometer assembly 15 having connector 13, and elongate member 16 coupled to follower assembly 14. As will be described in further detail to follow, commander unit 12 has a first knob 18 structured for causing longitudinal movement of elongate member 16 as indicated by arrow L, and a second knob 20 structured for causing rotational movement of elongate member 16 as indicated by arrow R. Thus, as those skilled in the art will appreciate, drive system 10 may be utilized to control the precise longitudinal and angular position of elongate member 16 relative to or within a particular location or element, such as generic mass M shown in broken lines proximate to follower assembly 14.

Potentiometer assembly 15 may be operably coupled to follower assembly 14 and configured to provide feedback regarding the longitudinal and angular position of elongate member 16 to a computer system or other processing means through connector 13. An external display may be operably coupled to the computer system or processing means in order to display longitudinal and rotational movement of elongate member 16 during operation of drive system 10. A display may alternatively be provided on commander unit 12 instead of (or in addition to) the external display as will be appreciated by those skilled in the art. In one exemplary embodiment, the longitudinal movement of elongate member 16 may be displayed as a numerical value (relative to a "zero" reference point) having any suitable unit, such as in millimeters. Furthermore, the rotational movement of elongate member 16 may be displayed in any suitable manner, such as by a number in a range between about +180 degrees and about −180 degrees surrounding a "zero" reference point. However, those skilled in the art will appreciate that the longitudinal and rotational movement of elongate member 16 may be displayed in numerous other ways and within numerous other ranges without departing from the intended scope of the present invention.

Figure 2A:
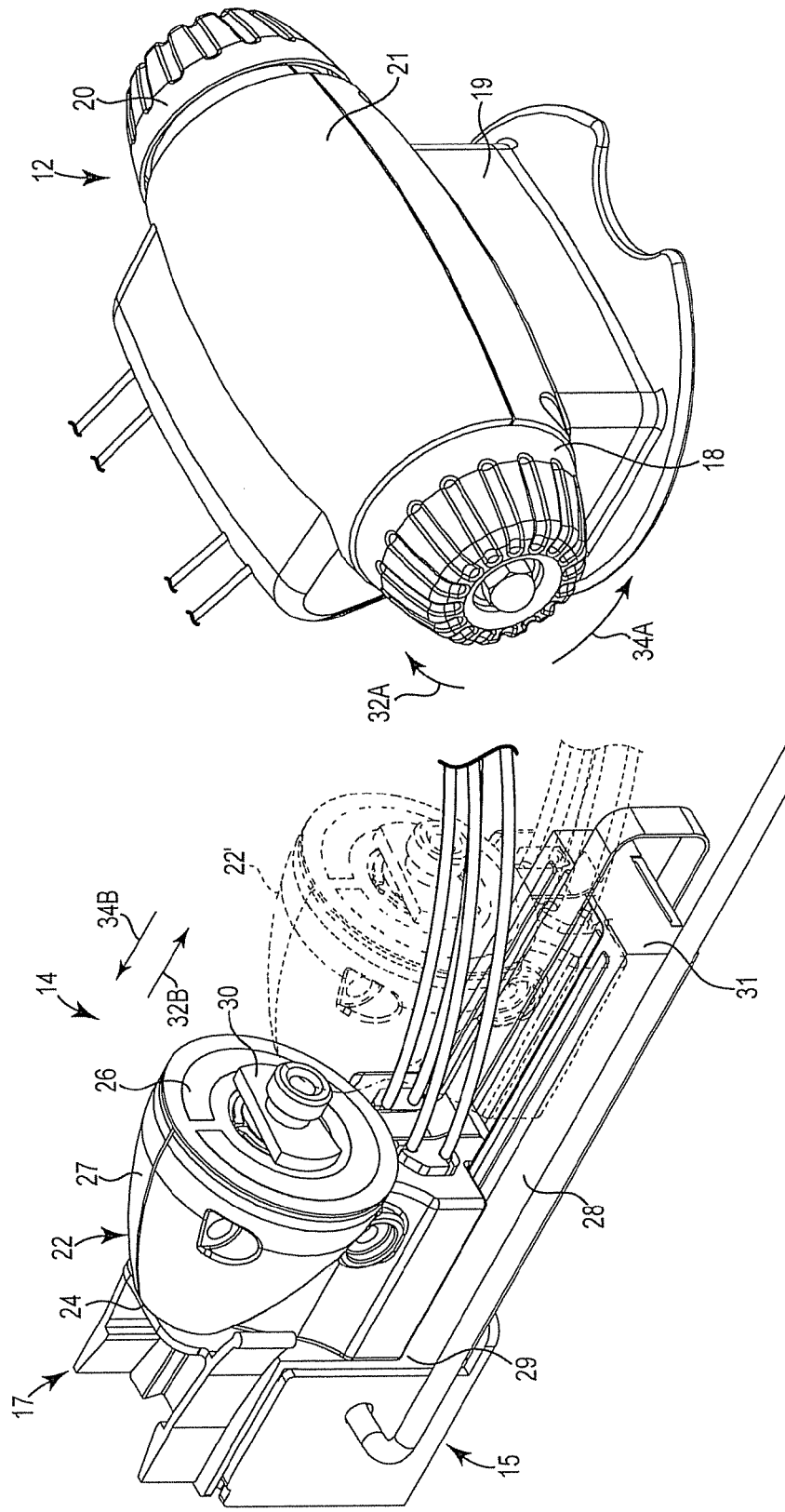
FIG. 2A is a perspective view of the commander unit and follower assembly of FIG. 1 illustrating rotation of a first knob to cause longitudinal movement of a follower device.

FIG. 2A is a perspective view of commander unit 12 and follower assembly 14 illustrating rotation of first knob 18 and the corresponding longitudinal movement of follower assembly 14. In particular, commander unit 12 includes a commander base 19 and a commander cover 21. Follower assembly 14 includes follower device 22 having a distal end 24 and a proximal end 26. Follower device 22 is encased by follower housing 27 and is operably coupled to guide rail 28 such that follower device 22 may be driven between a distal end 29 and a proximal end 31 of guide rail 28. Potentiometer assembly 15 is positioned at distal end 29 of guide rail 28, and adjacent to potentiometer assembly 15 is attachment means 17 for attaching follower assembly 14 to any suitable mount or support, such as an adjustable trajectory setting mount. As illustrated in FIG. 2A, attachment means 17 includes a "clip" type fastener structured to allow the attachment means to clip to a mount or support, although any suitable attachment means may be used.

Figure 2B:
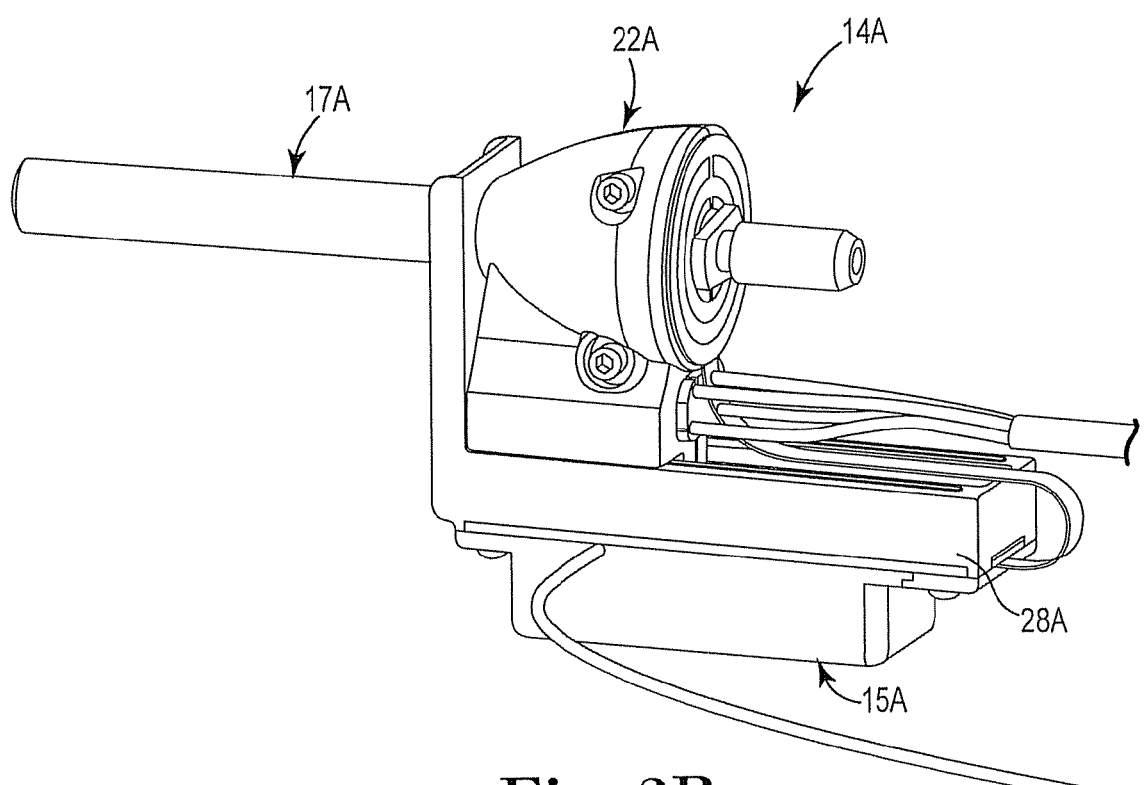
FIG. 2B is a perspective view of one exemplary alternative follower assembly in accordance with the present invention.

Although follower assembly 14 is illustrated in FIG. 2A as including a potentiometer assembly adjacent a distal end of a guide rail and attachment means that includes a "clip" type fastener, modifications may be made without departing from the intended scope of the present invention. For example, follower assembly 14A illustrated in FIG. 2B is one exemplary alternative embodiment of a follower assembly in accordance with the present invention. Particularly, follower assembly 14A includes components generally similar to those in follower assembly 14. However, potentiometer assembly 15A is located on a side of guide rail 28A opposite follower device 22A instead of at a distal end of guide rail 28A. Additionally, attachment means 17 has been replaced by an alternative attachment means 17A having a generally tubular member that may be structured to be received within a mount or support, such as an adjustable trajectory setting mount as discussed above. Thus, numerous alternative configurations of the follower assembly are contemplated as will be appreciated by those skilled in the art.

Turning again to follower assembly 14 of FIG. 2A, proximal end 26 of follower device 22 includes a rotatable alignment device 30 coupled thereto and structured to receive elongate member 16. Elongate member 16 has been omitted in FIG. 2A to provide a clearer view of the operation of commander unit 12 and follower assembly 14. However, as will be appreciated by those skilled in the art, elongate member 16 may be fixed within rotatable alignment device 30 such that longitudinal movement of follower device 22 and rotational movement of alignment device 30 is translated directly to elongate member 16 in order to control the longitudinal and rotational position of elongate member 16.

As generally illustrated in FIG. 2A, rotating first knob 18 in the direction indicated by arrow 32A may result in follower device 22 being driven longitudinally along guide rail 28 in the direction indicated by arrow 32B. This longitudinal movement is illustrated by follower device 22' shown in broken lines. Similarly, rotating first knob 18 in the direction indicated by arrow 34A may result in follower device 22 being driven longitudinally along guide rail 28 in the direction indicated by arrow 34B. Thus, the user may control the precise longitudinal position of follower device 22 along guide rail 28 based upon the amount that first knob 18 is rotated as well as the direction in which it is rotated.

Figure 3:
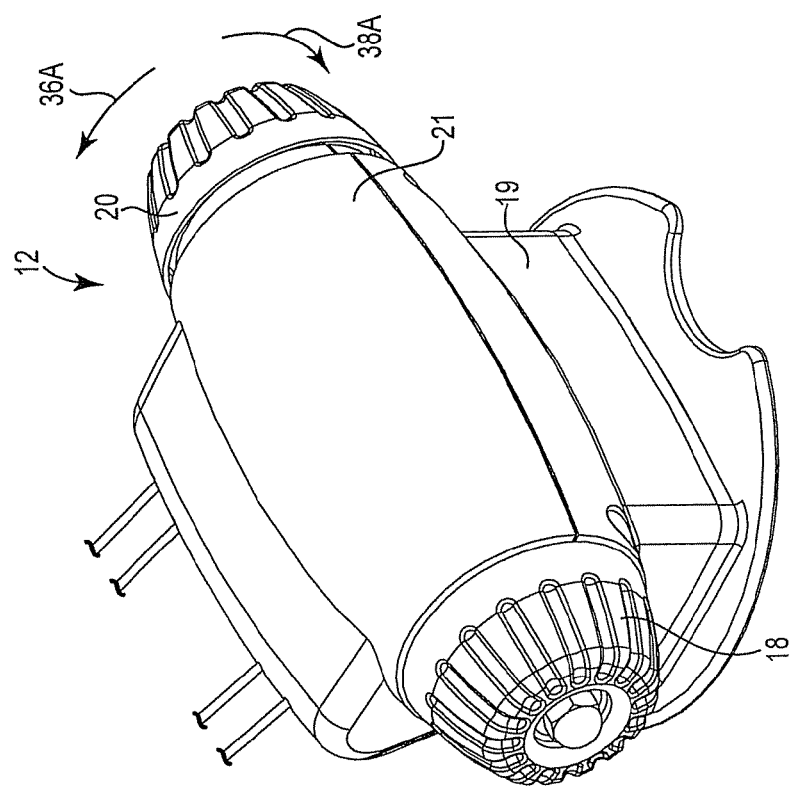
FIG. 3 is a perspective view of the commander unit and follower assembly of FIG. 1 illustrating rotation of a second knob to cause rotational movement of an alignment device on a proximal end of the follower device.
Figure 3:
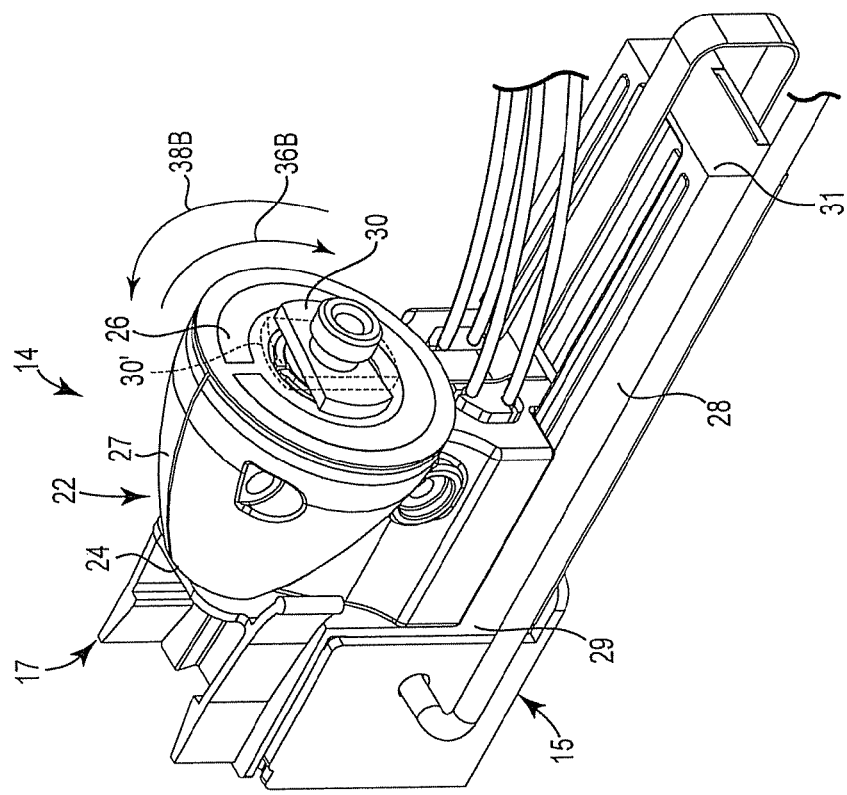

FIG. 3 is a perspective view of commander unit 12 and follower assembly 14 illustrating rotation of second knob 20 and the corresponding rotational movement of alignment device 30 on proximal end 26 of follower device 22. As stated above, because elongate member 16 is insertable through alignment device 30 and may be fixed thereto, rotational movement of alignment device 30 may cause elongate member 16 to rotate by a similar amount to control the rotational position and orientation of elongate member 16.

As generally illustrated in FIG. 3, rotating second knob 20 in the direction indicated by arrow 36A may result in alignment device 30 being rotated with respect to follower device 22 in the direction indicated by arrow 36B. This rotational movement is illustrated by alignment device 30' shown in broken lines. Similarly, rotating second knob 20 in the direction indicated by arrow 38A may result in alignment device 30 being rotated with respect to follower device 22 in the direction indicated by arrow 38B. Thus, the user may control the precise rotational position of alignment device 30 with respect to follower device 22 based upon the amount that second knob 20 is rotated as well as the direction in which it is rotated.

Figure 4:
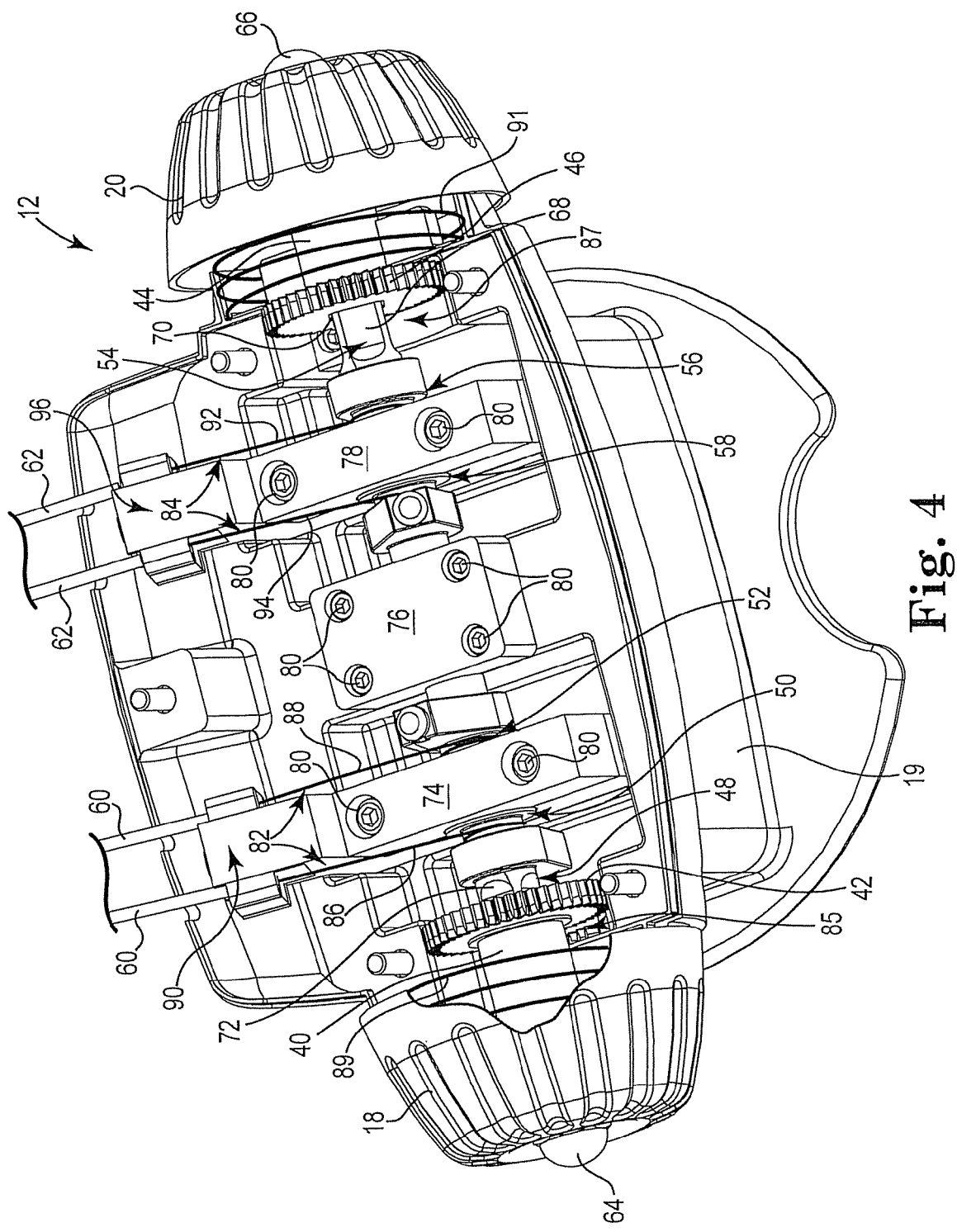
FIG. 4 is an enlarged perspective view of the commander unit with a commander cover removed to illustrate the internal components of the commander unit.

FIG. 4 is an enlarged perspective view of commander unit 12 with commander cover 21 removed to illustrate the internal components of commander unit 12. In particular, commander unit 12 includes first internal knob 40 having first knob gear 42, second internal knob 44 having second knob gear 46, first drive spool shaft 48 having first spool 50 and second spool 52, second drive spool shaft 54 having first spool 56 and second spool 58, a pair of wire sheaths 60 associated with first drive spool shaft 48, and a pair of wire sheaths 62 associated with second drive spool shaft 54. First internal knob 40 may be coupled to first knob 18 via bolt 64 inserted through an aperture in first knob 18 and into a threaded recess in an end of first internal knob 40. Similarly, second internal knob 44 may be coupled to second knob 20 via bolt 66 inserted through an aperture in second knob 20 and into a threaded recess in an end of second internal knob 44.

As shown in FIG. 4, second drive spool shaft 54 may include a generally square in cross-section end portion 68 that is structured to be received by and mate with a generally square aperture 70 in second knob gear 46 of second internal knob 44. The phrase "generally square" is intended to include embodiments that have both "sharp" and "rounded" corners, as illustrated in FIG. 4. In one exemplary embodiment, square aperture 70 may have approximately similar dimensions as end portion 68 such that a substantially tight connection is formed between second knob gear 46 and end portion 68. The combination of end portion 68 of second drive spool shaft 54 and square aperture 70 allows rotation of second knob 20 by the user to be transferred to second drive spool shaft 54. Similarly, first drive spool shaft 48 includes a generally square in cross-section end portion 72 that is structured to be received by and mate with a generally square aperture (not shown) in first knob gear 42 of first internal knob 40. Once again, the square aperture may have approximately similar dimensions as end potion 72 such that a substantially tight connection is formed between first knob gear 42 and end portion 72.

Although first and second drive spool shafts 48 and 54 have been described as including generally square end portions 72 and 68, respectively, that are configured to mate with generally square apertures, those skilled in the art will appreciate that the drive spool shafts may alternatively include end portions having numerous other cross-sectional shapes including, for example, triangles, rectangles, hexagons, and the like. Thus, any shape combination that will allow rotational movement to be transferred from a knob gear to a drive spool shaft is contemplated and within the intended scope of the present invention.

In addition to the connection to first knob gear 42 described above, first drive spool shaft 48 may be contained within commander unit 12 by first spool shaft top carrier 74 and drive shaft retainer 76. Similarly, in addition to the connection to second knob gear 46 described above, second drive spool shaft 54 may be contained within commander unit 12 by second spool shaft top carrier 78 and drive shaft retainer 76. As will be appreciated by those skilled in the art, first spool shaft top carrier 74, second spool shaft top carrier 78, and drive shaft retainer 76 function together with commander base 19 to form bushings for containing first and second drive spool shafts 48 and 54 and allowing rotation of the shafts. Once first and second drive spool shafts 48 and 54 are properly positioned within commander unit 12 during assembly, both first and second spool shaft top carriers 74 and 78, along with drive shaft retainer 76, may be fastened to commander base 19. In one exemplary embodiment, first spool shaft top carrier 74, second spool shaft top carrier 78, and drive shaft retainer 76 are fastened to commander base 19 with screws 80, although any suitable fastening means may be used as will be appreciated by those skilled in the art such as bolts or an adhesive. Those skilled in the art will also appreciate that first and second drive spool shafts 48 and 54 may be sufficiently contained by the bushings formed with first and second spool shaft top carriers 74 and 78 such that the use of drive shaft retainer 76 is not necessary. Thus, in an alternative embodiment drive shaft retainer 76 may be removed from commander unit 12 without departing from the spirit and scope of the present invention.

As illustrated in FIG. 4, drive system 10 further includes longitudinal movement wire 82 operably attached to first drive spool shaft 48 and rotational movement wire 84 operably attached to second drive spool shaft 54. In particular, a first end 86 of longitudinal movement wire 82 extends out of one of the wire sheaths 60 associated with first drive spool shaft 48 and wraps around first spool 50, while a second end 88 of longitudinal movement wire 82 extends out of the other one of the wire sheaths 60 and wraps around second spool 52. As further illustrated in FIG. 4, a first end 92 of rotational movement wire 84 extends out of one of the wire sheaths 62 associated with second drive spool shaft 54 and wraps around first spool 56, while a second end 94 of rotational movement wire 84 extends out of the other one of the wire sheaths 62 and wraps around second spool 58.

In order to prevent first and second knobs 18 and 20 from being rotated unintentionally and to lock them into place when not in use, drive system 10 also includes first and second locking devices 85 and 87. In particular, first locking device 85 is structured to engage first knob gear 42 in order to lock first knob 18, while second locking device 87 is structured to engage second knob gear 46 in order to lock second knob 20. Thus, first and second locking devices 85 and 87 serve as "safety" devices that minimize the possibility that the longitudinal and rotational positions of elongate member 16 may be unintentionally altered. As will be discussed in further detail to follow, an axial force must be applied to first knob 18 against the force of a first spring 89 disposed between first knob 18 and commander base 19 in order to disengage first locking device 85 and allow first knob 18 to be rotated, and thus allow the user to manipulate the longitudinal position of elongate member 16. Similarly, an axial force must also be applied to second knob 20 against the force of a second spring 91 disposed between second knob 20 and commander base 19 in order to disengage second locking device 87 and allow second knob 20 to be rotated, and thus allow the user to manipulate the rotational position of elongate member 16.

Optionally, as shown in FIG. 4, the pair of wire sheaths 60 associated with first drive spool shaft 48 may be coupled to first tension block assembly 90, while the pair of wire sheaths 62 associated with second drive spool shaft 54 may be coupled to second tension block assembly 96. Particularly, although first and second tension block assemblies 90 and 96 are not necessary components of the present invention, the tension block assemblies function to relieve tension placed on longitudinal and rotational movement wires 82 and 84, respectively, when the wires are wound onto and unwound from their respective drive spool shafts. One exemplary embodiment of a tension block assembly will be described below in reference to FIG. 5.

Figure 5:
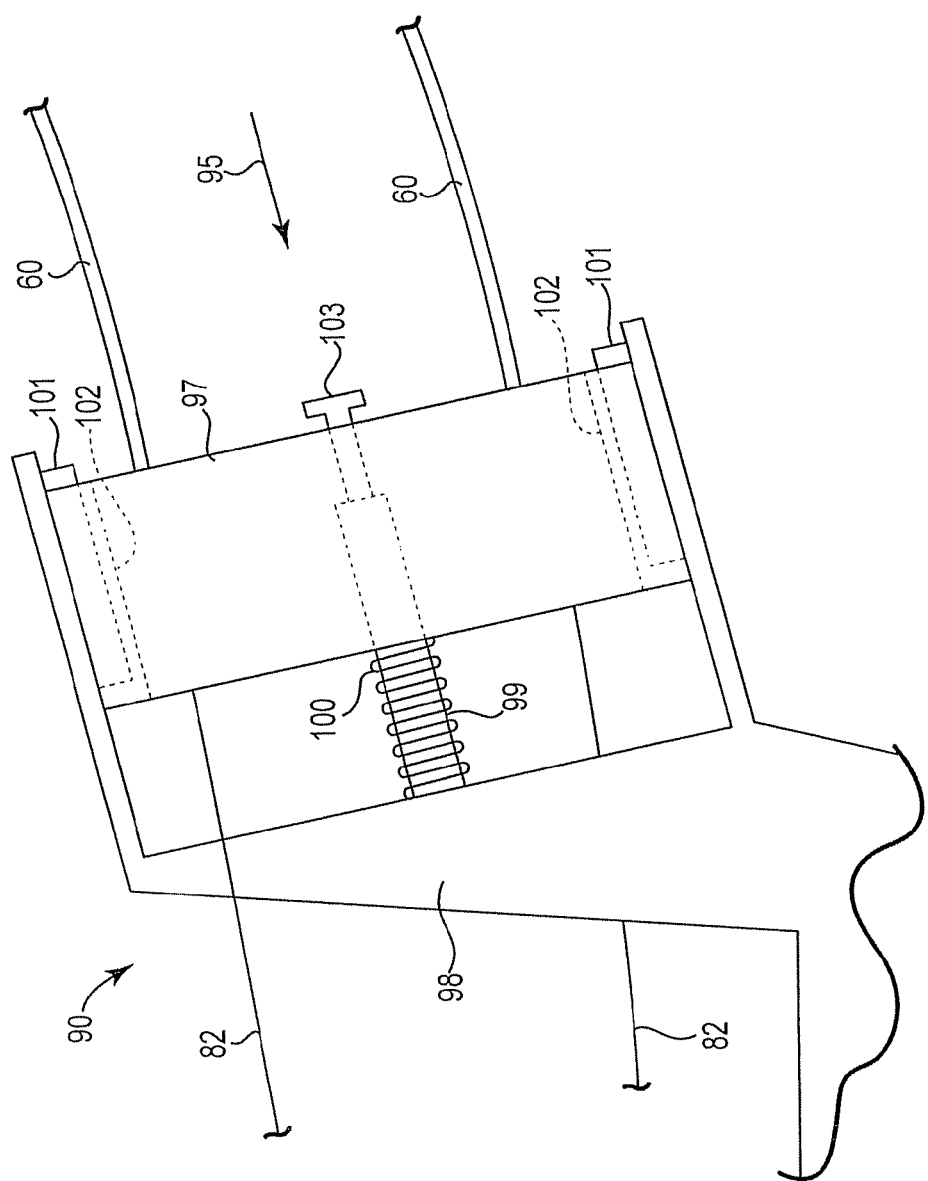
FIG. 5 is a diagram illustrating a side view of a first tension block assembly within the commander unit.

In particular, FIG. 5 is a diagram illustrating a side view of first tension block assembly 90. First tension block assembly 90 generally includes sheath connector block 97, sheath connector block holder 98, post member 99 structured to be inserted into an aperture through sheath connector block 97, and spring 100. Sheath connector block holder 98 includes a pair of flanges 101 structured to be received by a pair of slots 102 in sheath connector block 97. A fastener 103 couples sheath connector block 97 to post member 99 in order to limit the movement of sheath connector block 97 and prevent flanges 101 from being removed from slots 102. During operation of drive system 10, sheath connector block 97 may move in the direction indicated by arrow 95 as necessary in order to relieve tension placed on longitudinal movement wire 82 when the wire is being wound onto and unwound from first drive spool shaft 48. Thus, sheath connector block 97 is structured to travel in a direction that substantially coincides with the direction in which longitudinal movement wire 82 travels into and out of the commander unit 12. This minimizes the possibility that longitudinal movement wire 82 will break during operation of the drive system and provides for smoother rotation of first knob 18. Those skilled in the art will appreciate that the above discussion focused on first tension block assembly 90 merely for purposes of example and not limitation, and that second tension block assembly 96 may be designed in a similar manner.

Numerous alternative tension block assemblies may also be incorporated into commander unit 12 as will be appreciated by those skilled in the art. For example, in one alternative tension block assembly, the sheath connector block may be designed such that rather than traveling in a direction that substantially coincides with the direction of movement of longitudinal movement wire 82, the sheath connector block instead travels in a direction that is substantially perpendicular to the direction of movement of longitudinal movement wire 82. Thus, as longitudinal movement wire 82 "rides" on and is guided by the sheath connector block, the post and spring operably coupled to the sheath connector block allow the block to travel in a direction substantially perpendicular to the direction of travel of longitudinal movement wire 82 in order to minimize the tension placed on longitudinal movement wire 82 as the wire travels into and out of the commander unit 12.

Figure 6:
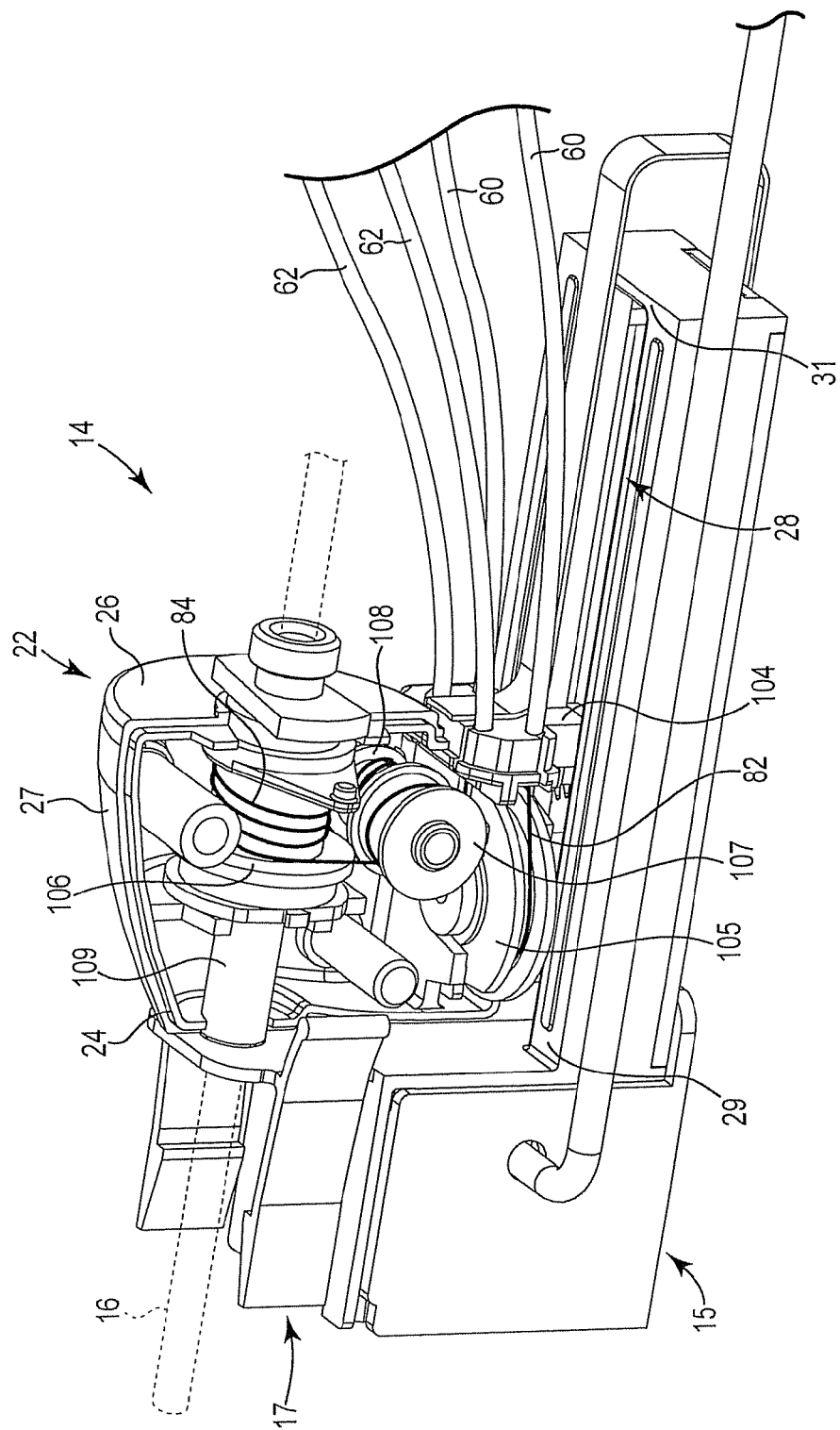
FIG. 6 is an enlarged perspective view of the follower assembly with a portion of the follower device housing removed in order to illustrate the internal components of the follower device.

FIG. 6 is an enlarged perspective view of follower assembly 14 with a portion of follower housing 27 removed in order to illustrate the internal components of follower device 22. In particular, follower device 22 includes rail follower member 104, longitudinal movement pulley 105, rotational movement pulley 106, first idler pulley 107, second idler pulley 108, and tubular member 109 for receiving elongate member 16. As illustrated in FIG. 6, rail follower member 104 is structured to be received by and ride within guide rail 28 as follower device 22 is being moved longitudinally along the rail. Longitudinal movement pulley 105 may be positioned adjacent the pair of wire sheaths 60 containing longitudinal movement wire 82. Longitudinal movement wire 82 extends out of a first one of the wire sheaths 60, wraps around longitudinal movement pulley 105, and once again enters a second one of the wire sheaths 60 where it returns to commander unit 12.

Rotational movement pulley 106 is coupled to or formed integral with tubular member 109 and alignment device 30. Thus, as rotational movement pulley 106 is rotated by rotational movement wire 84, the rotational movement is transferred to tubular member 109 and alignment device 30. First idler pulley 107 may be positioned adjacent a first one of the wire sheaths 62, while second idler pulley 108 may be positioned adjacent a second one of the wire sheaths 62. Rotational movement wire 84 extends out of the first one of the wire sheaths 62 and wraps around first idler pulley 107 prior to reaching and wrapping around rotational movement pulley 106. Rotational movement wire 84 then extends to and wraps around second idler pulley 108 prior to once again entering the second one of the wire sheaths 62 where it returns to commander unit 12.

Figure 7:
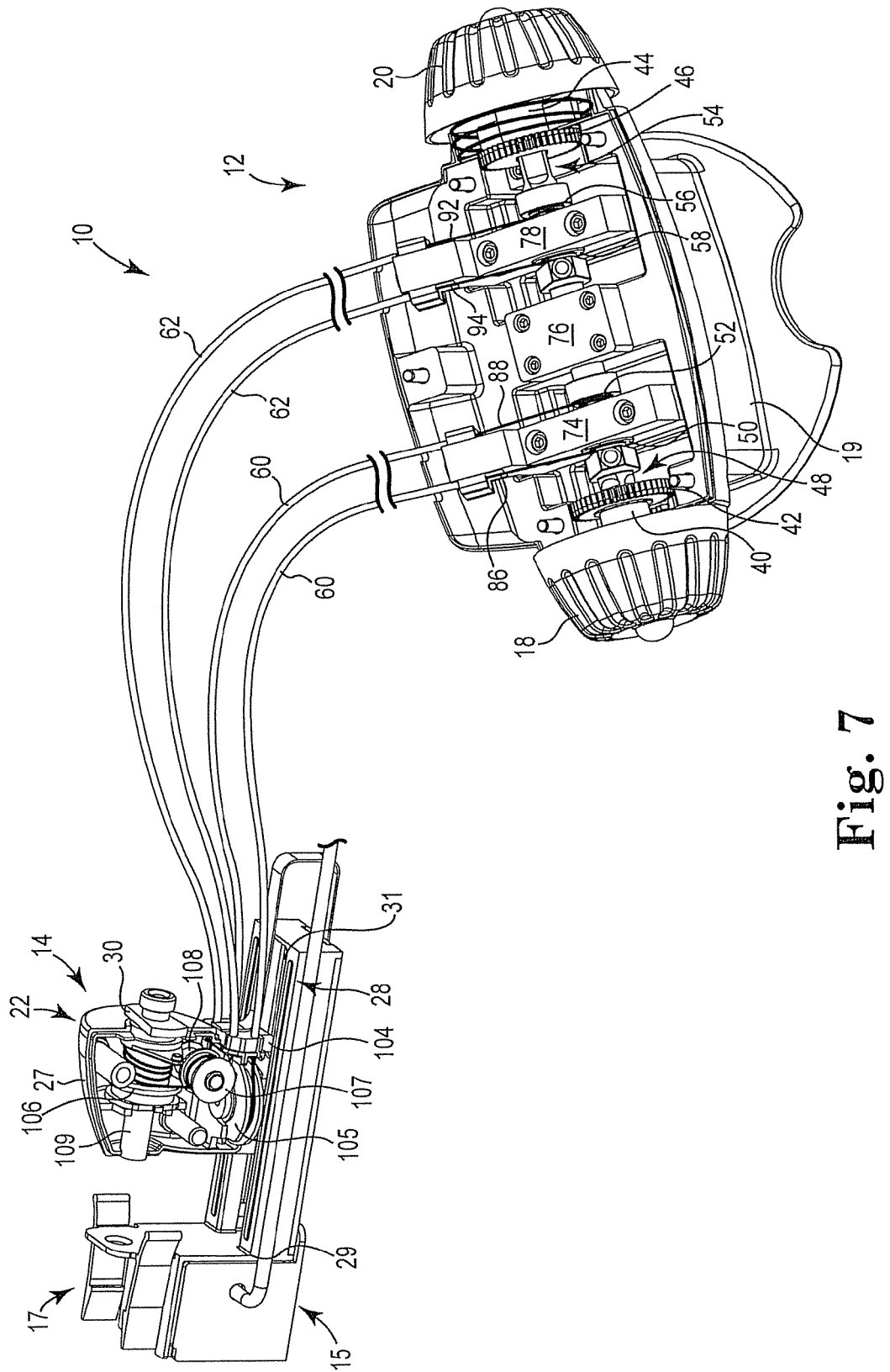
FIG. 7 is a perspective view of the drive system in accordance with the present invention wherein the follower device is shown in a "neutral" starting position.

FIG. 7 is a perspective view of drive system 10 with follower device 22 of follower assembly 14 shown in a "neutral" starting position. This neutral starting position of follower device 22, which is about midway between distal end 29 and proximal end 31 of guide rail 28, is defined merely for purposes of example and not limitation. Thus, operation of drive system 10 will be hereinafter described with reference to the neutral starting position illustrated in FIG. 7. However, those skilled in the art will appreciate that the starting position may be defined as some other location along guide rail 28 without departing from the intended scope of the present invention.

Figure 8A:
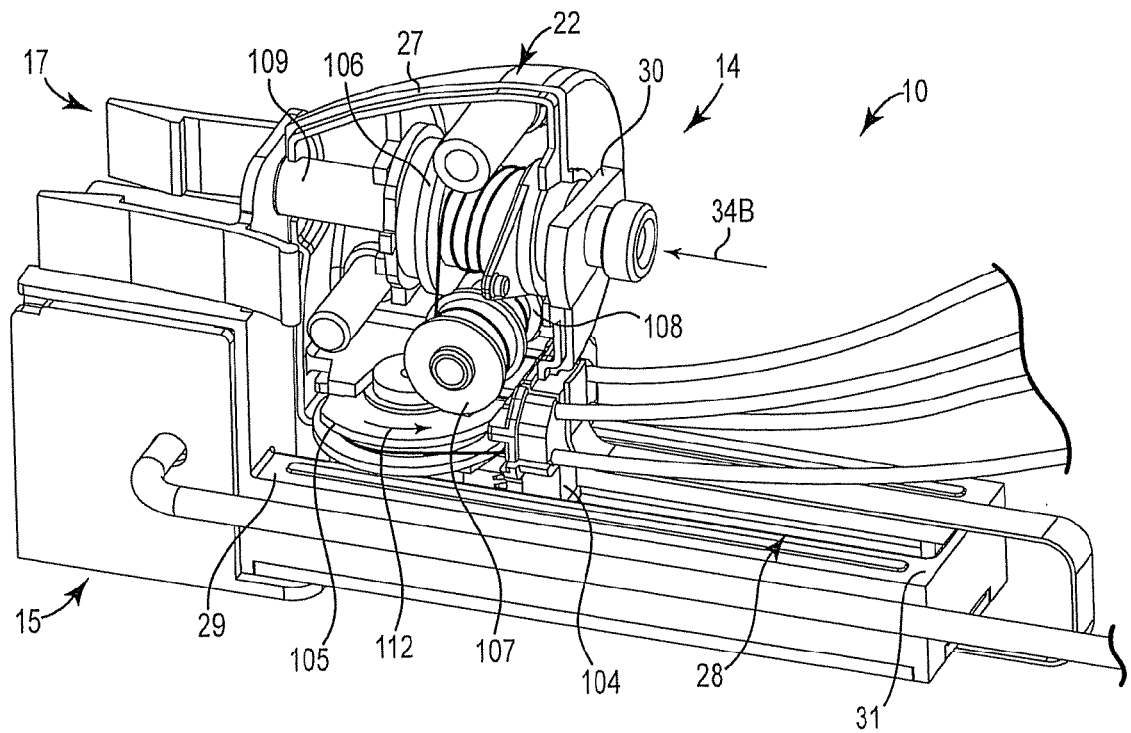
FIG. 8A is a perspective view of the drive system illustrating operation of the commander unit to drive the follower device longitudinally and in a distal direction.
Figure 8A:
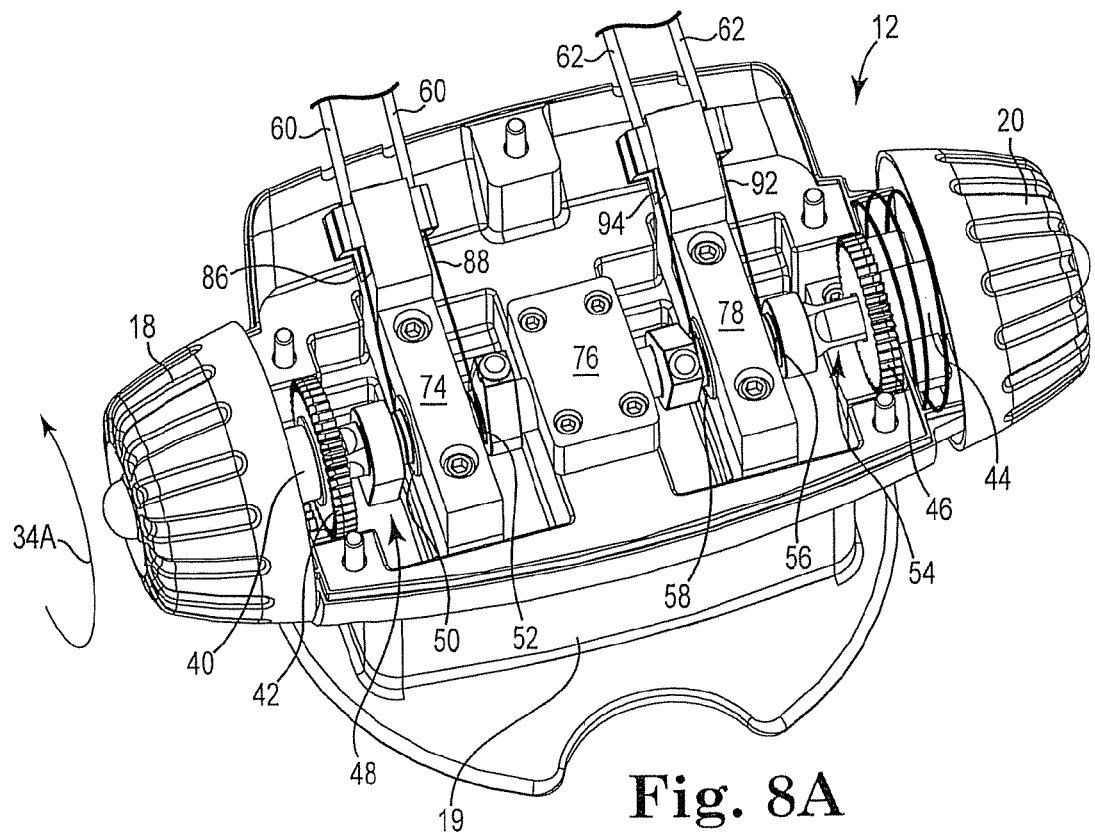

FIG. 8A is a perspective view of drive system 10 illustrating operation of commander unit 12 to drive follower device 22 longitudinally toward distal end 29 of guide rail 28. In particular, as shown in FIG. 8A, rotating first knob 18 in the direction indicated by arrow 34A drives follower device 22 longitudinally in the direction indicated by arrow 34B from the neutral starting position illustrated in FIG. 7 to a new position adjacent distal end 29 of guide rail 28. With reference to FIG. 1, the effect of driving follower device 22 longitudinally in the direction indicated by arrow 34B is to drive elongate member 16 into mass M (or further into mass M if elongate member 16 was already positioned within the mass).

As first knob 18 is rotated in the direction indicated by arrow 34A, first drive spool shaft 48 is also rotated in a similar direction due to the connection between end portion 72 of first drive spool shaft 48 and first knob gear 42 of first internal knob 40 as previously discussed in reference to FIG. 4. As a result, first end 86 of longitudinal movement wire 82 is further wound around first spool 50 of first drive spool shaft 48, while second end 88 of longitudinal movement wire 82 is further unwound from second spool 52. While first end 86 and second end 88 of longitudinal movement wire 82 are being correspondingly wound onto and unwound from first and second spools 50 and 52, respectively, longitudinal movement pulley 105 rotates in the direction indicated by arrow 112 in FIG. 8A as will be appreciated by those skilled in the art. As will be discussed in further detail in reference to FIG. 8B, the rotation of longitudinal movement pulley 105 in the direction indicated by arrow 112 causes follower device 22 to be driven longitudinally to the distal position shown in FIG. 8A.

Figure 8B:
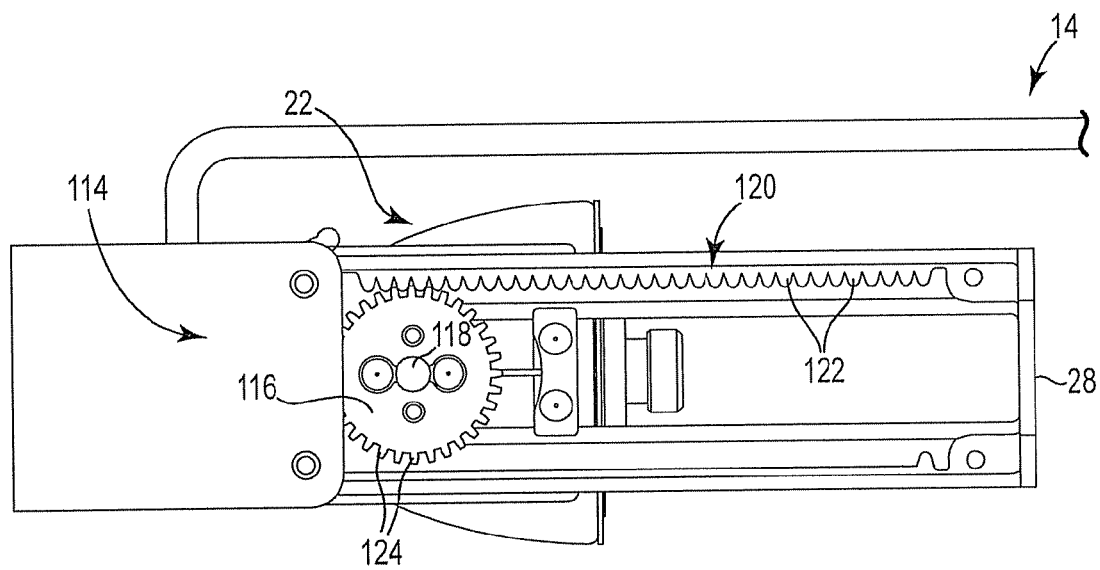
FIG. 8B is a diagram of an underside of the follower assembly illustrating movement of the follower device longitudinally and in the distal direction shown in FIG. 8A.

FIG. 8B is a diagram illustrating an underside 114 of follower assembly 14. As shown in FIG. 8B, follower assembly 14 further includes a follower gear 116 operably coupled to longitudinal movement pulley 105 via a suitable connecting means 118. Connecting means 118 is structured to couple the movement of longitudinal movement pulley 105 described in reference to FIG. 8A to follower gear 116. Thus, for example, as longitudinal movement pulley 105 is being rotated in the direction indicated by arrow 112 in FIG. 8A, follower gear 116 is also correspondingly being rotated in direction 112 due to follower gear 116 being operably coupled to longitudinal movement pulley 105 via connecting means 118.

The underside 114 of follower assembly 14 illustrates a gear track portion 120 of guide rail 28 having a plurality of teeth 122 structured to mate with a corresponding plurality of teeth 124 on follower gear 116. Thus, as follower gear 116 is being rotated by longitudinal movement pulley 105, teeth 124 on follower gear 116 engage teeth 122 on gear track 120 in order to drive follower gear 116, and thus follower device 22, longitudinally along gear track 120.

Figure 9B:
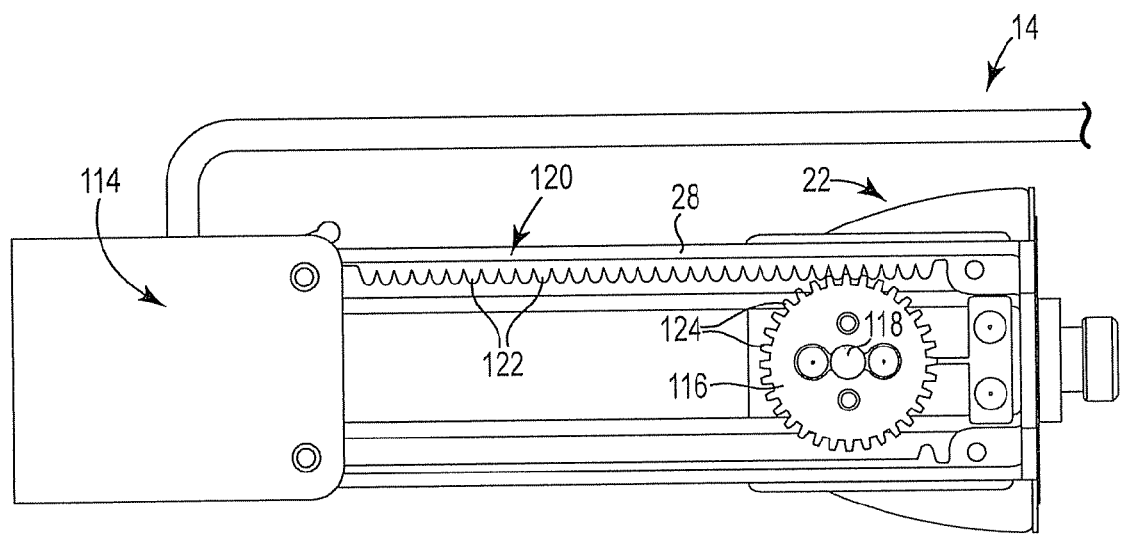
FIG. 9B is a diagram of the underside of the follower assembly illustrating movement of the follower device longitudinally and in the proximal direction shown in FIG. 9A.
Figure 9A:
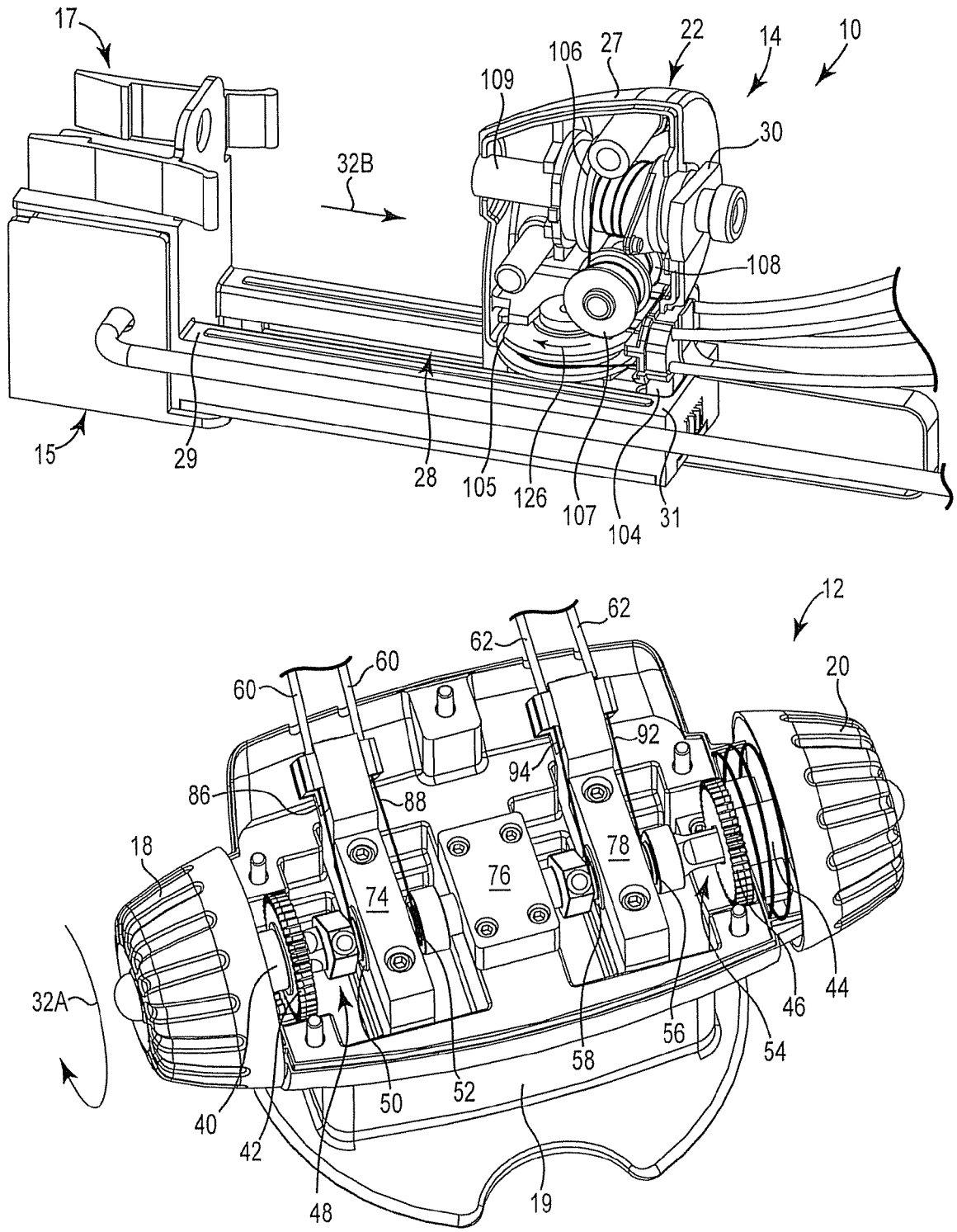
FIG. 9A is a perspective view of the drive system illustrating operation of commander unit to drive the follower device longitudinally and in a proximal direction.

FIG. 9A is a perspective view of drive system 10 illustrating operation of commander unit 12 to drive follower device 22 longitudinally toward proximal end 31 of guide rail 28. In particular, as shown in FIG. 9A, rotating first knob 18 in the direction indicated by arrow 32A drives follower device 22 longitudinally in the direction indicated by arrow 32B from the neutral starting position illustrated in FIG. 7 (or from, for example, the position illustrated in FIG. 8A) to a new position adjacent proximal end 31 of guide rail 28. With reference to FIG. 1, the effect of driving follower device 22 longitudinally in the direction indicated by arrow 32B may be to withdraw elongate member 16 from mass M.

Once again, rotating first knob 18 in the direction indicated by arrow 32A causes first drive spool shaft 48 to be rotated in a similar direction. As a result, second end 88 of longitudinal movement wire 82 is further wound around second spool 52 of first drive spool shaft 48, while first end 86 of longitudinal movement wire 82 is further unwound from first spool 50. While first end 86 and second end 88 of longitudinal movement wire 82 are being correspondingly unwound from and wound onto first and second spools 50 and 52, respectively, longitudinal movement pulley 105 rotates in the direction indicated by arrow 126 in FIG. 9A as will be appreciated by those skilled in the art. The rotation of longitudinal movement pulley 105 in the direction indicated by arrow 126 causes follower device 22 to be driven longitudinally to the proximal position shown in FIG. 9A.

FIG. 9B is a diagram illustrating underside 114 of guide rail portion 28 of follower assembly 14 after follower device 22 has been driven to proximal end 31 of guide rail 28. Because connecting means 118 couples the movement of longitudinal movement pulley 105 to follower gear 116, rotating pulley 105 in the direction indicated by arrow 126 causes a corresponding rotation of follower gear 116 in a similar direction. In particular, as follower gear 116 is being rotated by longitudinal movement pulley 105, teeth 124 on follower gear 116 engage teeth 122 on gear track 120 in order to drive follower gear 116, and thus follower device 22, longitudinally along gear track 120 to the proximal position illustrated in FIG. 9B.

Figure 10:
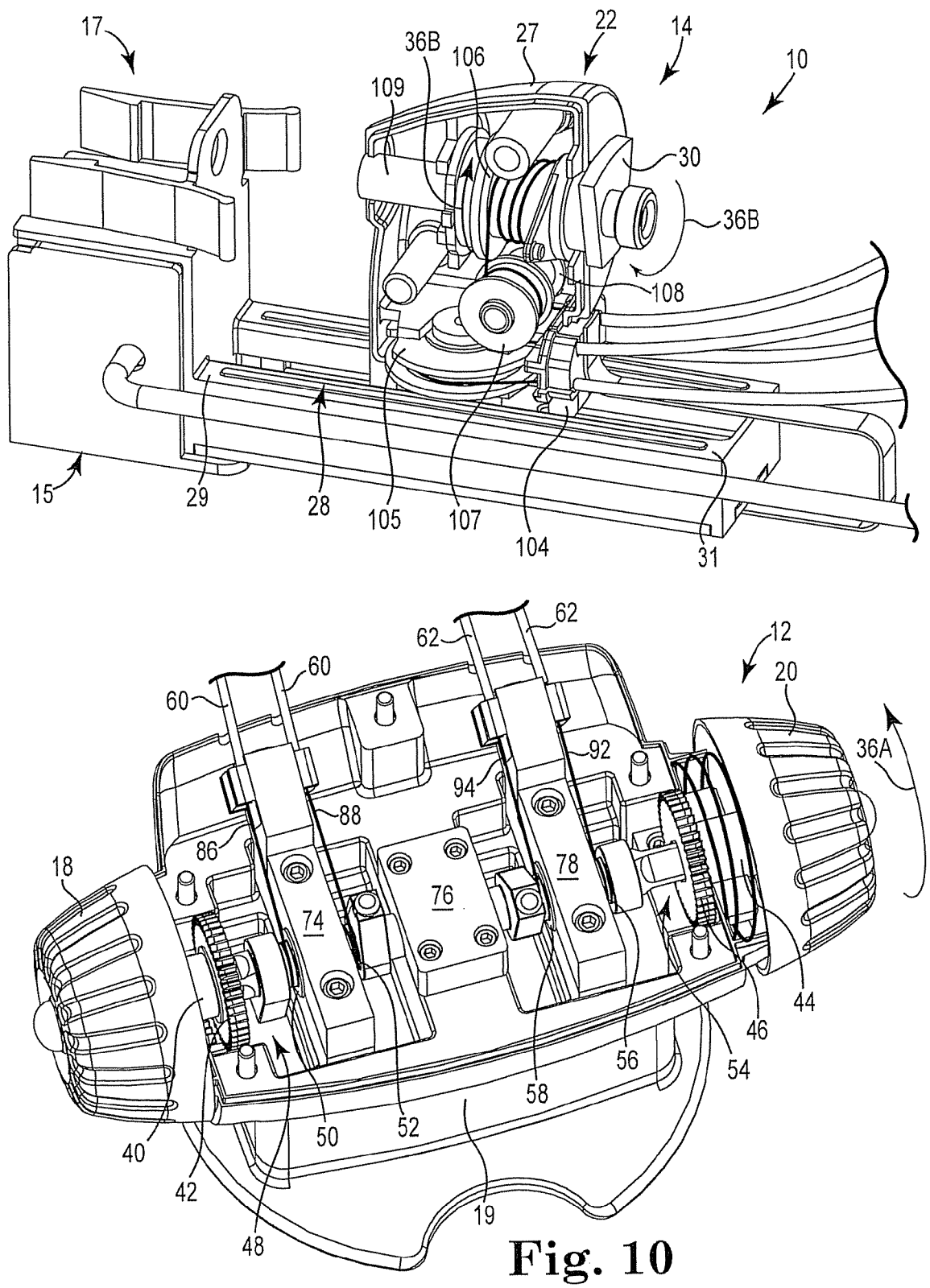
FIG. 10 is a perspective view of the drive system illustrating operation of the commander unit to rotate the alignment device in a clockwise direction as viewed from a proximal end of the follower device.

FIG. 10 is a perspective view of drive system 10 illustrating operation of commander unit 12 to rotate alignment device 30 in a clockwise direction as viewed from proximal end 26 of follower device 22. In particular, as shown in FIG. 10, rotating second knob 20 in the direction indicated by arrow 36A rotates alignment device 30 in the direction indicated by arrow 36B from the neutral starting position illustrated in FIG. 7. With reference to FIG. 1, the effect of rotating alignment device 30 in the direction indicated by arrow 36B is to rotate the attached elongate member 16 relative to mass M, which is stationary. As shown in FIG. 10, alignment device 30 has been rotated in a clockwise direction by approximately 90 degrees. However, one skilled in the art will appreciate that alignment device 30 may be rotated by any amount between about zero and 360 degrees.

As second knob 20 is rotated in the direction indicated by arrow 36A, second drive spool shaft 54 is also rotated in a similar direction due to the connection between end portion 68 of second drive spool shaft 54 and second knob gear 46 of second internal knob 44 as previously discussed in reference to FIG. 4. As a result, first end 92 of rotational movement wire 84 is further wound around first spool 56 of second drive spool shaft 54, while second end 94 of rotational movement wire 84 is further unwound from second spool 58. While first end 92 and second end 94 of rotational movement wire 84 are being correspondingly wound onto and unwound from first and second spools 56 and 58, respectively, rotational movement pulley 106 rotates in the direction indicated by arrow 36B in FIG. 10 as will be appreciated by those skilled in the art. Because rotational movement pulley 106 is coupled to or formed integral with alignment device 30, alignment device 30 is also rotated in the direction indicated by arrow 36B.

Figure 11:
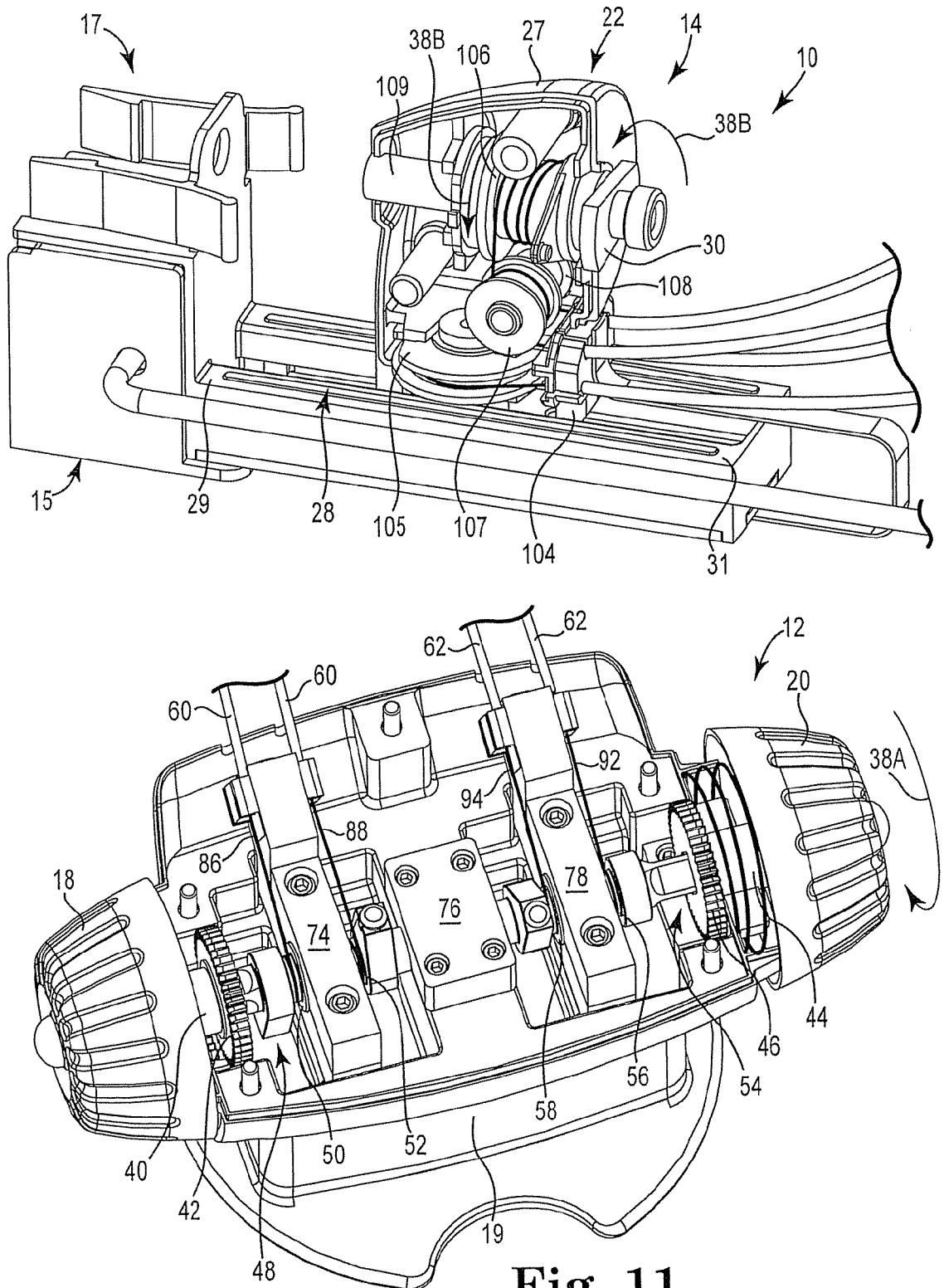
FIG. 11 is a perspective view of the drive system illustrating operation of the commander unit to rotate the alignment device in a counterclockwise direction as viewed from the proximal end of the follower device.

FIG. 11 is a perspective view of drive system 10 illustrating operation of commander unit 12 to rotate alignment device 30 in a counterclockwise direction as viewed from proximal end 26 of follower device 22. In particular, as illustrated in FIG. 11, rotating second knob 20 in the direction indicated by arrow 38A rotates alignment device 30 in the direction indicated by arrow 38B from the position shown in FIG. 10 back to the starting position shown in FIG. 7. Although alignment device 30 is illustrated as being rotated counterclockwise by approximately 90 degrees, one skilled in the art will appreciate that second knob 20 may be manipulated such that alignment device 30 is rotated by a different amount without departing from the intended scope of the present invention.

Once again, rotating second knob 20 in the direction indicated by arrow 38A causes second drive spool shaft 54 to be rotated in a similar direction. As a result, second end 94 of rotational movement wire 84 is further wound around second spool 58 of second drive spool shaft 54, while first end 92 of rotational movement wire 84 is further unwound from first spool 56. While first end 92 and second end 94 of rotational movement wire 84 are being correspondingly unwound from and wound onto first and second spools 56 and 58, respectively, rotational movement pulley 106 rotates in the direction indicated by arrow 38B in FIG. 11 as will be appreciated by those skilled in the art. Alignment device 30 is also rotated in the direction indicated by arrow 38B due to its attachment to rotational movement pulley 106.

Figure 12A:
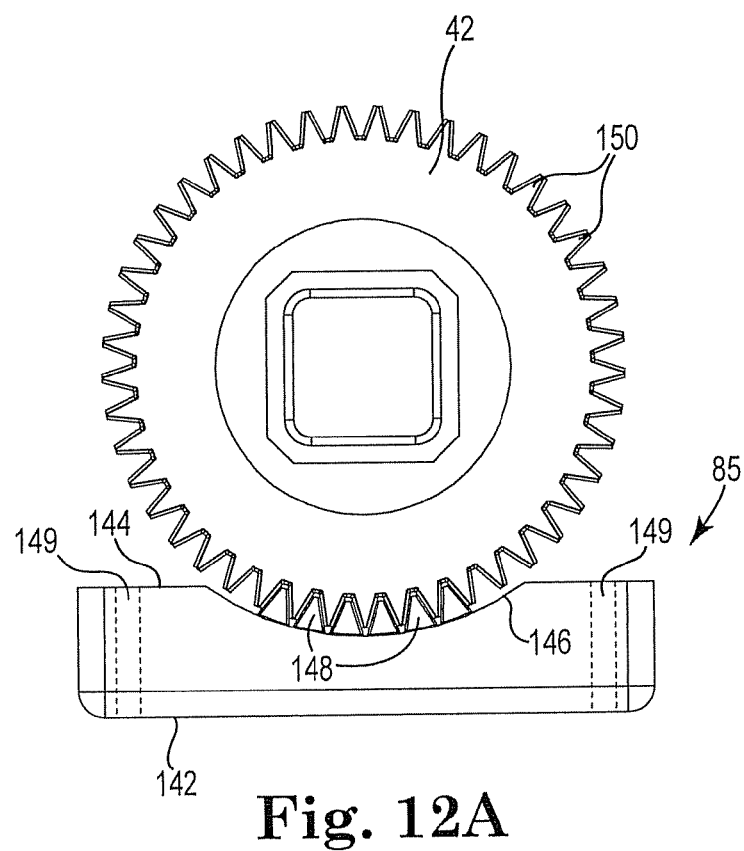
FIG. 12A is a diagram illustrating the structure of a first locking device coupled to the commander unit.

FIG. 12A is a diagram illustrating first locking device 85 introduced above in reference to FIG. 4 and structured to operate with first knob 18. Although commander unit 12 also includes second locking device 87 structured to operate with second knob 20, both first and second locking devices 85 and 87 operate substantially the same. Thus, while first locking device 85 is illustrated and described in detail, the discussion applies equally to second locking device 87 as well.

As illustrated in FIG. 12A, first locking device 85 includes bottom surface 142 structured to engage an inner surface of commander base 19 and a top surface 144 having a curved portion 146 with a plurality of locking teeth 148. Locking device 85 may be coupled to commander base 19 by any suitable means, such as with fasteners inserted through apertures 149. In another exemplary embodiment, locking device 85 may be formed integral with commander base 19 or coupled to commander base 19 with an adhesive. Locking teeth 148 are structured to engage a plurality of knob gear teeth 150 on first knob gear 42 when first knob 18 is in a "locked" position. In particular, first knob 18 is normally biased in the locked position by first spring 89, and must be moved against the spring force of first spring 89 to an "unlocked" position as illustrated in FIG. 12B prior to adjusting the longitudinal position of elongate member 16 in the manner previously described.

Figure 12B:
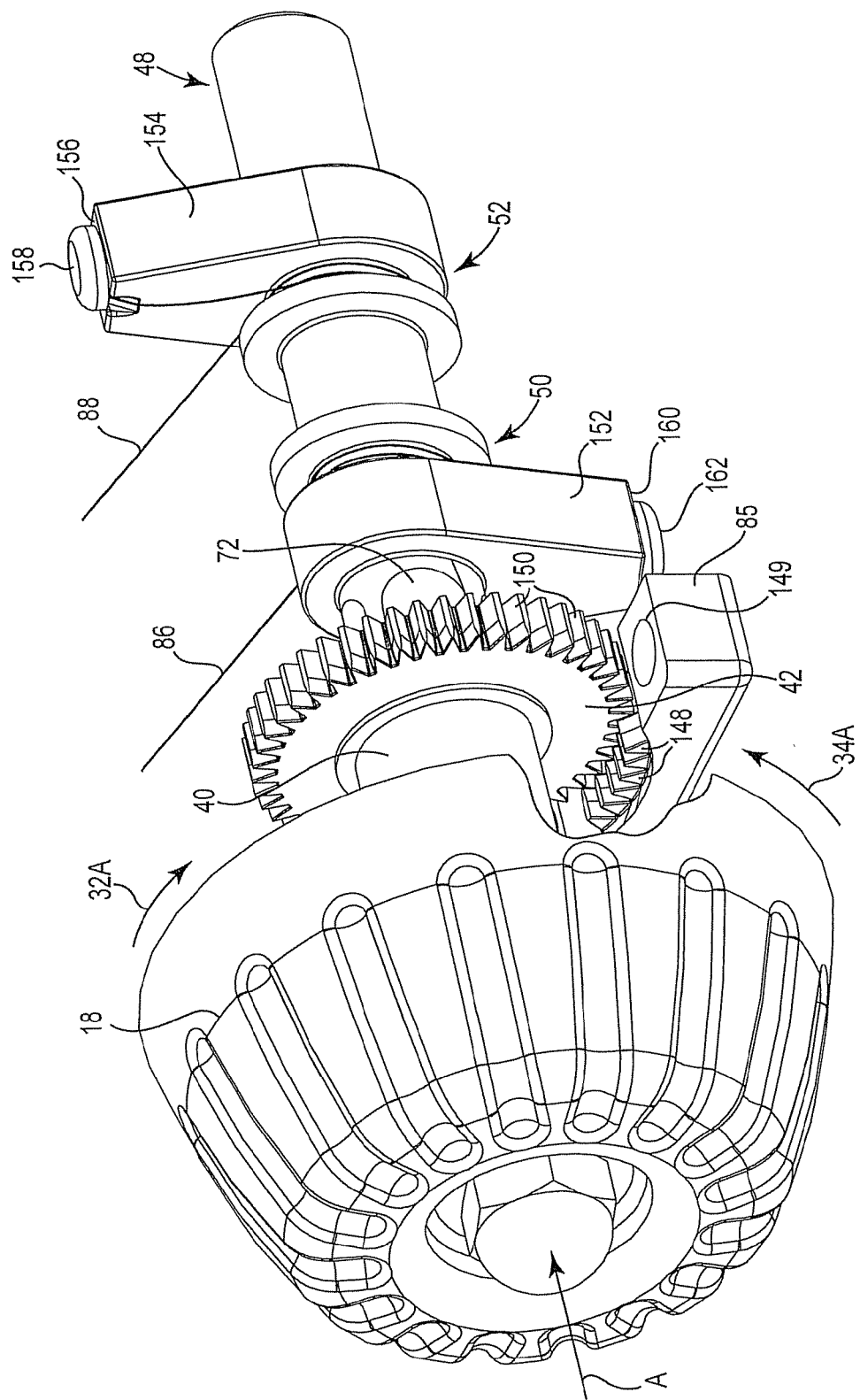
FIG. 12B is a perspective view of the first locking device illustrating the first knob in an unlocked position.

FIG. 12B is a perspective view of first knob 18 and first locking device 85 illustrating first knob 18 in the unlocked position. In particular, prior to rotating first knob 18 in either the direction indicated by arrow 32A or the direction indicated by arrow 34A as previously described in reference to FIGS. 2A, 8A, and 9A, first knob 18 must be moved to the unlocked position. First knob 18 may be moved from the locked position shown in FIG. 12A to the unlocked position shown in FIG. 12B by applying an axial force A to first knob 18, thereby disengaging knob gear teeth 150 on first knob gear 42 from locking teeth 148 on first locking device 85. Once knob gear teeth 150 are disengaged from locking teeth 148, the user may freely rotate first knob 18 in the directions indicated by arrows 32A and 34A as long as the axial force A is maintained. When further manipulation of the longitudinal position of elongate member 16 is no longer necessary, the user may simply discontinue applying the axial force A, and first spring member 89 will force knob gear teeth 150 back into engagement with locking teeth 148, thereby preventing further rotation of first knob 18. As one skilled in the art will appreciate, the longitudinal position of elongate member 16 may be manipulated further by once again applying axial force A to first knob 18 and rotating the knob.

As further illustrated in FIG. 12B, first drive spool shaft 48 may include first shaft flange 152 adjacent first spool 50 and second shaft flange 154 adjacent second spool 52. In particular, second end 88 of longitudinal movement wire 82 may extend along second shaft flange 154 and be fastened to an end portion 156 thereof with fastening means 158. Similarly, although not visible in FIG. 12B, first end 86 of longitudinal movement wire 82 may extend along first shaft flange 152 and be fastened to and end portion 160 thereof with fastening means 162.

Workers skilled in the art will appreciate that although drive system 10 has been described with reference to rotational movements of first and second knobs 18 and 20 that result in longitudinal and rotational movements in specific directions, the drive system may be modified such that rotation of the knobs instead result in movement in the opposite direction without departing from the intended scope of the present invention. Thus, the specific direction in which elongate member 16 moves as a result of manipulating knobs 18 and 20 is not an essential component of the present invention.

Although the present invention has been described with reference to preferred embodiments, workers skilled in the art will recognize that changes may be made in form and detail without departing from the spirit and scope of the invention.

What is claimed is:

1. A drive system, comprising:
a base unit including first and second spools to spool, respectively, first and second wires; and
an assembly extending in a longitudinal direction and coupled to the base unit by the first and second wires, the assembly including a mount coupled to the assembly, and the mount including a rotatable portion and first and second wire supports that support, respectively, the first and second wires, wherein:
the rotatable portion is rotatable about an axis of rotation that extends in the longitudinal direction, and is structured to hold and rotate an elongated member about the axis of rotation,
the first wire support is coupled to the mount and the assembly such that a movement of the first wire along the first wire support causes the mount to move along the assembly in the longitudinal direction, and
the second wire support is coupled to the mount and the rotatable portion such that a movement of the second wire along the second wire support causes the rotatable portion to rotate about the axis of rotation of the rotatable portion, and wherein:
the base unit includes first and second spool shafts for each of the first and second spools, such that rotational movements of the first and second spools cause rotations of the first and second spool shafts;
opposing ends of the first wire are connected to the first and second spools shafts for the first spool, such that the rotational movement of the first spool causes, concurrently, both the first and second spool shafts for the first spool to rotate, causing the first and second spool shafts for the first spool to respectively wind and unwind the first wire; and
opposing ends of the second wire are connected to the first and second spools shafts for the second spool, such that the rotational movement of the second spool causes, concurrently, both the first and second spool shafts for the second spool to rotate, causing the first and second spool shafts for the second spool to respectively wind and unwind the second wire.

2. The drive system of claim 1, wherein:
the first wire support includes a first pulley and the assembly includes a guide rail that includes a track that extends in the longitudinal direction and that is coupled to the first pulley; and
the first wire winds around the first pulley such that winding and unwinding of the first wire causes the first pulley to rotate and move the mount in the longitudinal direction along the track of the guide rail.

3. The drive system of claim 2, wherein the first pulley has an axis of rotation that is perpendicular to the rotational axis of the rotatable portion and that is rotatably connected to a housing of the mount.

4. The drive system of claim 1, wherein:
the second wire support includes a second pulley that surrounds a portion of the rotatable portion such that the second pulley has an axis of rotation that is the same as the axis of rotation of the rotatable portion;
the mount includes an idler support; and
the second wire enters the mount, winds around the idler support, and then winds around the second pulley, such that winding and unwinding of the second wire causes the second pulley to rotate and move the rotatable portion in a rotational direction about the rotational axis of the rotatable portion.

5. The drive system of claim 4, wherein the idler support includes an idler pulley that has an axis of rotation that is perpendicular to the rotational axis of the rotatable portion and that is rotatably connected to a housing of the mount.

6. The drive system of claim 1, wherein:
the first wire support includes a gear and the assembly includes a gear track to engage with the gear of the first wire support;
the first wire winds around the first wire support such that winding and unwinding of the first wire causes the gear to rotate and move the mount in the longitudinal direction along the gear track;
the second wire support includes a guide shaft that surrounds a portion of the rotatable portion such that the guide shaft has an axis of rotation that is the same as the axis of rotation of the rotatable portion;
the mount includes an idler support; and
the second wire enters the mount, winds around the idler support, and then winds around the guide shaft, such that winding and unwinding of the second wire causes the guide shaft to rotate and move the rotatable portion in a rotational direction about the rotational axis of the rotatable portion.

7. The drive system of claim 1, further comprising:
wire sheaths that cover the first and second wires for at least portions of the first and second wires that extend between the base unit and the assembly, wherein
the wire sheaths are flexible conduits that allow the first and second wires to travel therein, and that are fixedly secured to the base unit and the assembly.

8. The drive system of claim 7, wherein:
the base unit includes first and second tension blocks for the first and second wires;
respective sheath connector blocks of the first and second tension blocks are attached to respective wire sheaths of the first and second wires;
the sheath connector blocks are elastically secured to the first and second tension blocks; and
the first and second tension blocks relieve tension placed on the first and second wires, during movements thereof, by allowing travel between the wire sheaths and the first and second tension blocks, via the sheath connector blocks.

9. The drive system of claim 7, wherein the base unit and the assembly are flexibly directly connected to each other by only the first and second wires and the wire sheaths.

10. The drive system of claim 1, wherein:
the base unit further includes a gear coupled to each of the first and second spools, and
the gear for each of the first and second spools is configured to releasably engage respective gear teeth to respectively control respective rotational movement of the first and second spools.

11. The drive system of claim 10, wherein the first and second spools are axially moveable to engage and disengage the gear teeth.

12. The drive system of claim 1, wherein the assembly includes an alignment guide that includes an alignment hole that is coaxial with the rotatable portion of the mount.

13. The drive system of claim 1, wherein the assembly includes a potentiometer assembly that includes an electrical connector to provide feedback regarding a longitudinal and angular position of the elongate member.

14. The drive system of claim 1, further comprising the elongated member.

15. The drive system of claim 1, wherein the first and second spools include respective rotatable knobs that rotate about respective first and second axes.

16. The drive system of claim 15, wherein the first and second axes coincide and are separated.

17. The drive system of claim 1, wherein:
the rotational movement of the first spool causes only the longitudinal movement of the mount and the rotatable portion in the longitudinal direction; and
the rotational movement of the second spool causes only the rotational movement of the rotatable portion.

18. The drive system of claim 1, wherein:
the rotational movement of the first spool causes the longitudinal movement of the mount and the rotatable portion in the longitudinal direction in one of opposing forward and backward directions coinciding with the longitudinal direction based on a direction of the rotational movement of the first spool; and
the rotational movement of the second spool causes the rotational movement of the rotatable portion in one of opposing clockwise and counter-clockwise directions about the rotational axis of the rotatable portion based on a direction of the rotational movement of the second spool.

19. The drive system of claim 1, wherein the assembly is magnetic resonance imaging (MRI) compatible.

20. The drive system of claim 1, wherein the coupling of the first and second wires between the base unit and the assembly provides a structure in which the base unit can be physically displaced, relative to the assembly, without causing the longitudinal movement of the mount and the rotatable portion in the longitudinal direction, and without causing the rotational movement of the rotatable portion.

21. A method for a drive system,
the drive system comprising:
a base unit including first and second spools to spool, respectively, first and second wires, and first and second spool shafts for each of the first and second spools, such that rotational movements of the first and second spools cause rotations of the first and second spool shafts, wherein opposing ends of the first wire are connected to the first and second spools shafts for the first spool, such that the rotational movement of the first spool causes, concurrently, both the first and second spool shafts for the first spool to rotate, causing the first and second spool shafts for the first spool to respectively wind and unwind the first wire; and opposing ends of the second wire are connected to the first and second spools shafts for the second spool, such that the rotational movement of the second spool causes, concurrently, both the first and second spool shafts for the second spool to rotate, causing the first and second spool shafts for the second spool to respectively wind and unwind the second wire; and
an assembly extending in a longitudinal direction and coupled to the base unit by the first and second wires, the assembly including a mount coupled to the assembly, and the mount including a rotatable portion and first and second wire supports that support, respectively, the first and second wires, wherein:
the rotatable portion is rotatable about an axis of rotation that extends in the longitudinal direction, and is structured to hold and rotate an elongated member about the axis of rotation,
the first wire support is coupled to the mount and the assembly such that a movement of the first wire along the first wire support causes the mount to move along the assembly in the longitudinal direction, and the second wire support is coupled to the mount and the rotatable portion such that a movement of the second wire along the second wire support causes the rotatable portion to rotate about the axis of rotation of the rotatable portion; and the method comprising:

rotating the first spool to drive the mount in one of opposing forward and backward directions coinciding with the longitudinal direction based on a direction of the rotating of the first spool; and rotating the second spool to rotate the rotatable portion in one of opposing clockwise and counter-clockwise directions about the rotational axis of the rotatable portion based on a direction of the rotating of the second spool.

22. The method of claim 21, wherein:

the base unit further includes a gear coupled to each of the first and second spools, and the gear for each of the first and second spools is configured to releasably engage respective gear teeth to control rotational movement of, respectively, the first and second spools;

the method further comprising:

axially displacing one of the first and second spools to disengage the one of the first and second spools from the respective gear teeth to allow rotating of the one of the first and second spools.

23. The method of claim 21, wherein:

the drive system includes the elongated member, the rotating the first spool drives the elongated member in the one of opposing forward and backward directions coinciding with the longitudinal direction based on the direction of the rotating of the first spool, and the rotating the second spool rotates the elongated member in the one of opposing clockwise and counter-clockwise directions about the rotational axis of the rotatable portion based on the direction of the rotating of the second spool.

* * * * *